US011642396B2

(12) United States Patent
Carter et al.

(10) Patent No.: US 11,642,396 B2
(45) Date of Patent: May 9, 2023

(54) METHOD OF REDUCING ANTIGENIC DRIFT OR REASSORTMENT OF VIRUSES IN A HOST ANIMAL USING α INTERFERON

(71) Applicant: AIM ImmunoTech Inc., Ocala, FL (US)

(72) Inventors: William A. Carter, Ocala, FL (US); David R. Strayer, Ocala, FL (US)

(73) Assignee: AIM ImmunoTech Inc., Ocala, FL (US)

( * ) Notice: Subject to any disclaimer, the term of this patent is extended or adjusted under 35 U.S.C. 154(b) by 0 days.

(21) Appl. No.: 14/913,562

(22) PCT Filed: Aug. 21, 2014

(86) PCT No.: PCT/US2014/052079

§ 371 (c)(1),
(2) Date: Feb. 22, 2016

(87) PCT Pub. No.: WO2015/027056

PCT Pub. Date: Feb. 26, 2015

(65) Prior Publication Data

US 2016/0199449 A1 Jul. 14, 2016

Related U.S. Application Data

(60) Provisional application No. 61/868,292, filed on Aug. 21, 2013.

(51) Int. Cl.

| | |
|---|---|
| ***A61K 49/00*** | (2006.01) |
| ***A61K 39/145*** | (2006.01) |
| ***A61K 38/21*** | (2006.01) |
| ***A61K 31/713*** | (2006.01) |
| ***C12Q 1/70*** | (2006.01) |

(52) U.S. Cl.

CPC .......... *A61K 38/212* (2013.01); *A61K 31/713* (2013.01); *C12Q 1/701* (2013.01)

(58) Field of Classification Search

None

See application file for complete search history.

(56) References Cited

FOREIGN PATENT DOCUMENTS

WO WO 2006/082435 8/2006

OTHER PUBLICATIONS

Penski et al., Highly Pathogenic Avian Influenza Viruses Do Not Inhibit Interferon Synthesis in Infected Chickens but Can Override the Interferon-Induced Antiviral State, 2011, Journal of Virology, vol. 85, No. 15, pp. 7730-7741.*

Strayer et al., Protection from pulmonary tissue damage associated with infection of cynomolgus macaques by highly pathogenic avian influenza virus (H5N1) by low dose natural human IFN-a administered to the buccal mucosa, Antiviral Research, 2014, vol. 110, pp. 175-180.*

International Search Report for PCT/US2014/052079, dated Nov. 3, 2014, 4 pages.

Written Opinion of the ISA for PCT/US2014/052079, dated Nov. 3, 2014, 5 pages.

Yen et al., "Resistance to Neuraminidase Inhibitors Conferred by an R292K Mutation in a Human Influenza Virus H7N9 Isolate Can Be Masked by a Mixed R/K Viral Population", MBIO, vol. 4, No. 4, Jul. 16, 2013, pp. e00396-13.

Zhou et al., Biological Features of Novel Avian Influenza A (H7N9) Virus, Nature, vol. 499, No. 7459, Jul. 3, 2013, pp. 500-503.

Liu et al., "Original and Diversity of Novel Avian Influenza A H7N9 Viruses Causing Human Infection: Phylogenetic, Structural, and Coalescent Analyses", The Lancet, vol. 381, No. 9881, Jun. 1, 2013, pp. 1926-1932.

* cited by examiner

*Primary Examiner* — Benjamin P Blumel

(74) *Attorney, Agent, or Firm* — Studebaker & Brackett PC

(57) ABSTRACT

This disclosures relates to methods of preventing or reducing antigenic drift, viral reassortment and symptoms of wild-type and mutant influenza viruses in a host animal by determining if a host animal has been exposed to or infected by an avian influenza virus, and administering to the exposed host animal α-interferon.

6 Claims, 3 Drawing Sheets

Specification includes a Sequence Listing.

Tamiflu:

Anhui-NA-292R

Tamiflu-sensitive strain

MOI=0.01
A549 cell

Tamiflu:

Shanghai-NA-292k

Tamiflu-resistant strain

MOI=0.01
A549 cell

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 1
tttttttttt tttttttttt tttt 24

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
ggccagtgaa ttgtaatacg actcactata gggaggcggt tttttttttt tttttttttt 60
ttt 63

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 3
tttttttttt tttttttt 18

<210> SEQ ID NO 4
<211> LENGTH: 40000
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(40000)
<223> OTHER INFORMATION: Inosine
<220> FEATURE:
<221> NAME/KEY: misc_feature
<222> LOCATION: (1)..(40000)
<223> OTHER INFORMATION: This sequence may encompass 40-40,000
nucleotides

<400> SEQUENCE: 4
nnnnnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720

-continued

```
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnnnnn nnnnnnnnnn nnnnnnnnnn   2700
nnnnnnnnnn nnnnnnnnnn nnnnnnnnnn nnnnnnnnnn nnnnnnnnnn nnnnnnnnnn   2760
nnnnnnnnnn nnnnnnnnnn nnnnnnnnnn nnnnnnnnnn nnnnnnnnnn nnnnnnnnnn   2820
nnnnnnnnnn nnnnnnnnnn nnnnnnnnnn nnnnnnnnnn nnnnnnnnnn nnnnnnnnnn   2880
nnnnnnnnnn nnnnnnnnnn nnnnnnnnnn nnnnnnnnnn nnnnnnnnnn nnnnnnnnnn   2940
nnnnnnnnnn nnnnnnnnnn nnnnnnnnnn nnnnnnnnnn nnnnnnnnnn nnnnnnnnnn   3000
nnnnnnnnnn nnnnnnnnnn nnnnnnnnnn nnnnnnnnnn nnnnnnnnnn nnnnnnnnnn   3060
```

-continued

```
nnnnnnnnnn nnnnnnnnnn nnnnnnnnnn nnnnnnnnnn nnnnnnnnnn nnnnnnnnnn   3120
nnnnnnnnnn nnnnnnnnnn nnnnnnnnnn nnnnnnnnnn nnnnnnnnnn nnnnnnnnnn   3180
nnnnnnnnnn nnnnnnnnnn nnnnnnnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn nnnnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnnnn nnnnnnnnnn   3840
nnnnnnnnnn nnnnnnnnnn nnnnnnnnnn nnnnnnnnnn nnnnnnnnnn nnnnnnnnnn   3900
nnnnnnnnnn nnnnnnnnnn nnnnnnnnnn nnnnnnnnnn nnnnnnnnnn nnnnnnnnnn   3960
nnnnnnnnnn nnnnnnnnnn nnnnnnnnnn nnnnnnnnnn nnnnnnnnnn nnnnnnnnnn   4020
nnnnnnnnnn nnnnnnnnnn nnnnnnnnnn nnnnnnnnnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnnnnnn nnnnnnnnnn nnnnnnnnnn nnnnnnnnnn nnnnnnnnnn   4200
nnnnnnnnnn nnnnnnnnnn nnnnnnnnnn nnnnnnnnnn nnnnnnnnnn nnnnnnnnnn   4260
nnnnnnnnnn nnnnnnnnnn nnnnnnnnnn nnnnnnnnnn nnnnnnnnnn nnnnnnnnnn   4320
nnnnnnnnnn nnnnnnnnnn nnnnnnnnnn nnnnnnnnnn nnnnnnnnnn nnnnnnnnnn   4380
nnnnnnnnnn nnnnnnnnnn nnnnnnnnnn nnnnnnnnnn nnnnnnnnnn nnnnnnnnnn   4440
nnnnnnnnnn nnnnnnnnnn nnnnnnnnnn nnnnnnnnnn nnnnnnnnnn nnnnnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnnnnnnnnn nnnnnnnnnn nnnnnnnnnn nnnnnnnnnn nnnnnnnnnn nnnnnnnnnn   4740
nnnnnnnnnn nnnnnnnnnn nnnnnnnnnn nnnnnnnnnn nnnnnnnnnn nnnnnnnnnn   4800
nnnnnnnnnn nnnnnnnnnn nnnnnnnnnn nnnnnnnnnn nnnnnnnnnn nnnnnnnnnn   4860
nnnnnnnnnn nnnnnnnnnn nnnnnnnnnn nnnnnnnnnn nnnnnnnnnn nnnnnnnnnn   4920
nnnnnnnnnn nnnnnnnnnn nnnnnnnnnn nnnnnnnnnn nnnnnnnnnn nnnnnnnnnn   4980
nnnnnnnnnn nnnnnnnnnn nnnnnnnnnn nnnnnnnnnn nnnnnnnnnn nnnnnnnnnn   5040
nnnnnnnnnn nnnnnnnnnn nnnnnnnnnn nnnnnnnnnn nnnnnnnnnn nnnnnnnnnn   5100
nnnnnnnnnn nnnnnnnnnn nnnnnnnnnn nnnnnnnnnn nnnnnnnnnn nnnnnnnnnn   5160
nnnnnnnnnn nnnnnnnnnn nnnnnnnnnn nnnnnnnnnn nnnnnnnnnn nnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnn nnnnnnnnnn nnnnnnnnnn nnnnnnnnnn   5400
nnnnnnnnnn nnnnnnnnnn nnnnnnnnnn nnnnnnnnnn nnnnnnnnnn nnnnnnnnnn   5460
```

-continued nnnnnnnnnn nnnnnnnnnn nnnnnnnnnn nnnnnnnnnn nnnnnnnnnn nnnnnnnnnn 5520
nnnnnnnnnn nnnnnnnnnn nnnnnnnnnn nnnnnnnnnn nnnnnnnnnn nnnnnnnnnn 5580
nnnnnnnnnn nnnnnnnnnn nnnnnnnnnn nnnnnnnnnn nnnnnnnnnn nnnnnnnnnn 5640
nnnnnnnnnn nnnnnnnnnn nnnnnnnnnn nnnnnnnnnn nnnnnnnnnn nnnnnnnnnn 5700
nnnnnnnnnn nnnnnnnnnn nnnnnnnnnn nnnnnnnnnn nnnnnnnnnn nnnnnnnnnn 5760
nnnnnnnnnn nnnnnnnnnn nnnnnnnnnn nnnnnnnnnn nnnnnnnnnn nnnnnnnnnn 5820
nnnnnnnnnn nnnnnnnnnn nnnnnnnnnn nnnnnnnnnn nnnnnnnnnn nnnnnnnnnn 5880
nnnnnnnnnn nnnnnnnnnn nnnnnnnnnn nnnnnnnnnn nnnnnnnnnn nnnnnnnnnn 5940
nnnnnnnnnn nnnnnnnnnn nnnnnnnnnn nnnnnnnnnn nnnnnnnnnn nnnnnnnnnn 6000
nnnnnnnnnn nnnnnnnnnn nnnnnnnnnn nnnnnnnnnn nnnnnnnnnn nnnnnnnnnn 6060
nnnnnnnnnn nnnnnnnnnn nnnnnnnnnn nnnnnnnnnn nnnnnnnnnn nnnnnnnnnn 6120
nnnnnnnnnn nnnnnnnnnn nnnnnnnnnn nnnnnnnnnn nnnnnnnnnn nnnnnnnnnn 6180
nnnnnnnnnn nnnnnnnnnn nnnnnnnnnn nnnnnnnnnn nnnnnnnnnn nnnnnnnnnn 6240
nnnnnnnnnn nnnnnnnnnn nnnnnnnnnn nnnnnnnnnn nnnnnnnnnn nnnnnnnnnn 6300
nnnnnnnnnn nnnnnnnnnn nnnnnnnnnn nnnnnnnnnn nnnnnnnnnn nnnnnnnnnn 6360
nnnnnnnnnn nnnnnnnnnn nnnnnnnnnn nnnnnnnnnn nnnnnnnnnn nnnnnnnnnn 6420
nnnnnnnnnn nnnnnnnnnn nnnnnnnnnn nnnnnnnnnn nnnnnnnnnn nnnnnnnnnn 6480
nnnnnnnnnn nnnnnnnnnn nnnnnnnnnn nnnnnnnnnn nnnnnnnnnn nnnnnnnnnn 6540
nnnnnnnnnn nnnnnnnnnn nnnnnnnnnn nnnnnnnnnn nnnnnnnnnn nnnnnnnnnn 6600
nnnnnnnnnn nnnnnnnnnn nnnnnnnnnn nnnnnnnnnn nnnnnnnnnn nnnnnnnnnn 6660
nnnnnnnnnn nnnnnnnnnn nnnnnnnnnn nnnnnnnnnn nnnnnnnnnn nnnnnnnnnn 6720
nnnnnnnnnn nnnnnnnnnn nnnnnnnnnn nnnnnnnnnn nnnnnnnnnn nnnnnnnnnn 6780
nnnnnnnnnn nnnnnnnnnn nnnnnnnnnn nnnnnnnnnn nnnnnnnnnn nnnnnnnnnn 6840
nnnnnnnnnn nnnnnnnnnn nnnnnnnnnn nnnnnnnnnn nnnnnnnnnn nnnnnnnnnn 6900
nnnnnnnnnn nnnnnnnnnn nnnnnnnnnn nnnnnnnnnn nnnnnnnnnn nnnnnnnnnn 6960
nnnnnnnnnn nnnnnnnnnn nnnnnnnnnn nnnnnnnnnn nnnnnnnnnn nnnnnnnnnn 7020
nnnnnnnnnn nnnnnnnnnn nnnnnnnnnn nnnnnnnnnn nnnnnnnnnn nnnnnnnnnn 7080
nnnnnnnnnn nnnnnnnnnn nnnnnnnnnn nnnnnnnnnn nnnnnnnnnn nnnnnnnnnn 7140
nnnnnnnnnn nnnnnnnnnn nnnnnnnnnn nnnnnnnnnn nnnnnnnnnn nnnnnnnnnn 7200
nnnnnnnnnn nnnnnnnnnn nnnnnnnnnn nnnnnnnnnn nnnnnnnnnn nnnnnnnnnn 7260
nnnnnnnnnn nnnnnnnnnn nnnnnnnnnn nnnnnnnnnn nnnnnnnnnn nnnnnnnnnn 7320
nnnnnnnnnn nnnnnnnnnn nnnnnnnnnn nnnnnnnnnn nnnnnnnnnn nnnnnnnnnn 7380
nnnnnnnnnn nnnnnnnnnn nnnnnnnnnn nnnnnnnnnn nnnnnnnnnn nnnnnnnnnn 7440
nnnnnnnnnn nnnnnnnnnn nnnnnnnnnn nnnnnnnnnn nnnnnnnnnn nnnnnnnnnn 7500
nnnnnnnnnn nnnnnnnnnn nnnnnnnnnn nnnnnnnnnn nnnnnnnnnn nnnnnnnnnn 7560
nnnnnnnnnn nnnnnnnnnn nnnnnnnnnn nnnnnnnnnn nnnnnnnnnn nnnnnnnnnn 7620
nnnnnnnnnn nnnnnnnnnn nnnnnnnnnn nnnnnnnnnn nnnnnnnnnn nnnnnnnnnn 7680
nnnnnnnnnn nnnnnnnnnn nnnnnnnnnn nnnnnnnnnn nnnnnnnnnn nnnnnnnnnn 7740
nnnnnnnnnn nnnnnnnnnn nnnnnnnnnn nnnnnnnnnn nnnnnnnnnn nnnnnnnnnn 7800

-continued

```
nnnnnnnnnn nnnnnnnnnn nnnnnnnnnn nnnnnnnnnn nnnnnnnnnn nnnnnnnnnn   7860
nnnnnnnnnn nnnnnnnnnn nnnnnnnnnn nnnnnnnnnn nnnnnnnnnn nnnnnnnnnn   7920
nnnnnnnnnn nnnnnnnnnn nnnnnnnnnn nnnnnnnnnn nnnnnnnnnn nnnnnnnnnn   7980
nnnnnnnnnn nnnnnnnnnn nnnnnnnnnn nnnnnnnnnn nnnnnnnnnn nnnnnnnnnn   8040
nnnnnnnnnn nnnnnnnnnn nnnnnnnnnn nnnnnnnnnn nnnnnnnnnn nnnnnnnnnn   8100
nnnnnnnnnn nnnnnnnnnn nnnnnnnnnn nnnnnnnnnn nnnnnnnnnn nnnnnnnnnn   8160
nnnnnnnnnn nnnnnnnnnn nnnnnnnnnn nnnnnnnnnn nnnnnnnnnn nnnnnnnnnn   8220
nnnnnnnnnn nnnnnnnnnn nnnnnnnnnn nnnnnnnnnn nnnnnnnnnn nnnnnnnnnn   8280
nnnnnnnnnn nnnnnnnnnn nnnnnnnnnn nnnnnnnnnn nnnnnnnnnn nnnnnnnnnn   8340
nnnnnnnnnn nnnnnnnnnn nnnnnnnnnn nnnnnnnnnn nnnnnnnnnn nnnnnnnnnn   8400
nnnnnnnnnn nnnnnnnnnn nnnnnnnnnn nnnnnnnnnn nnnnnnnnnn nnnnnnnnnn   8460
nnnnnnnnnn nnnnnnnnnn nnnnnnnnnn nnnnnnnnnn nnnnnnnnnn nnnnnnnnnn   8520
nnnnnnnnnn nnnnnnnnnn nnnnnnnnnn nnnnnnnnnn nnnnnnnnnn nnnnnnnnnn   8580
nnnnnnnnnn nnnnnnnnnn nnnnnnnnnn nnnnnnnnnn nnnnnnnnnn nnnnnnnnnn   8640
nnnnnnnnnn nnnnnnnnnn nnnnnnnnnn nnnnnnnnnn nnnnnnnnnn nnnnnnnnnn   8700
nnnnnnnnnn nnnnnnnnnn nnnnnnnnnn nnnnnnnnnn nnnnnnnnnn nnnnnnnnnn   8760
nnnnnnnnnn nnnnnnnnnn nnnnnnnnnn nnnnnnnnnn nnnnnnnnnn nnnnnnnnnn   8820
nnnnnnnnnn nnnnnnnnnn nnnnnnnnnn nnnnnnnnnn nnnnnnnnnn nnnnnnnnnn   8880
nnnnnnnnnn nnnnnnnnnn nnnnnnnnnn nnnnnnnnnn nnnnnnnnnn nnnnnnnnnn   8940
nnnnnnnnnn nnnnnnnnnn nnnnnnnnnn nnnnnnnnnn nnnnnnnnnn nnnnnnnnnn   9000
nnnnnnnnnn nnnnnnnnnn nnnnnnnnnn nnnnnnnnnn nnnnnnnnnn nnnnnnnnnn   9060
nnnnnnnnnn nnnnnnnnnn nnnnnnnnnn nnnnnnnnnn nnnnnnnnnn nnnnnnnnnn   9120
nnnnnnnnnn nnnnnnnnnn nnnnnnnnnn nnnnnnnnnn nnnnnnnnnn nnnnnnnnnn   9180
nnnnnnnnnn nnnnnnnnnn nnnnnnnnnn nnnnnnnnnn nnnnnnnnnn nnnnnnnnnn   9240
nnnnnnnnnn nnnnnnnnnn nnnnnnnnnn nnnnnnnnnn nnnnnnnnnn nnnnnnnnnn   9300
nnnnnnnnnn nnnnnnnnnn nnnnnnnnnn nnnnnnnnnn nnnnnnnnnn nnnnnnnnnn   9360
nnnnnnnnnn nnnnnnnnnn nnnnnnnnnn nnnnnnnnnn nnnnnnnnnn nnnnnnnnnn   9420
nnnnnnnnnn nnnnnnnnnn nnnnnnnnnn nnnnnnnnnn nnnnnnnnnn nnnnnnnnnn   9480
nnnnnnnnnn nnnnnnnnnn nnnnnnnnnn nnnnnnnnnn nnnnnnnnnn nnnnnnnnnn   9540
nnnnnnnnnn nnnnnnnnnn nnnnnnnnnn nnnnnnnnnn nnnnnnnnnn nnnnnnnnnn   9600
nnnnnnnnnn nnnnnnnnnn nnnnnnnnnn nnnnnnnnnn nnnnnnnnnn nnnnnnnnnn   9660
nnnnnnnnnn nnnnnnnnnn nnnnnnnnnn nnnnnnnnnn nnnnnnnnnn nnnnnnnnnn   9720
nnnnnnnnnn nnnnnnnnnn nnnnnnnnnn nnnnnnnnnn nnnnnnnnnn nnnnnnnnnn   9780
nnnnnnnnnn nnnnnnnnnn nnnnnnnnnn nnnnnnnnnn nnnnnnnnnn nnnnnnnnnn   9840
nnnnnnnnnn nnnnnnnnnn nnnnnnnnnn nnnnnnnnnn nnnnnnnnnn nnnnnnnnnn   9900
nnnnnnnnnn nnnnnnnnnn nnnnnnnnnn nnnnnnnnnn nnnnnnnnnn nnnnnnnnnn   9960
nnnnnnnnnn nnnnnnnnnn nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
```

-continued nnnnnnnnnn nnnnnnnnnn nnnnnnnnnn nnnnnnnnnn nnnnnnnnnn nnnnnnnnnn 10260
nnnnnnnnnn nnnnnnnnnn nnnnnnnnnn nnnnnnnnnn nnnnnnnnnn nnnnnnnnnn 10320
nnnnnnnnnn nnnnnnnnnn nnnnnnnnnn nnnnnnnnnn nnnnnnnnnn nnnnnnnnnn 10380
nnnnnnnnnn nnnnnnnnnn nnnnnnnnnn nnnnnnnnnn nnnnnnnnnn nnnnnnnnnn 10440
nnnnnnnnnn nnnnnnnnnn nnnnnnnnnn nnnnnnnnnn nnnnnnnnnn nnnnnnnnnn 10500
nnnnnnnnnn nnnnnnnnnn nnnnnnnnnn nnnnnnnnnn nnnnnnnnnn nnnnnnnnnn 10560
nnnnnnnnnn nnnnnnnnnn nnnnnnnnnn nnnnnnnnnn nnnnnnnnnn nnnnnnnnnn 10620
nnnnnnnnnn nnnnnnnnnn nnnnnnnnnn nnnnnnnnnn nnnnnnnnnn nnnnnnnnnn 10680
nnnnnnnnnn nnnnnnnnnn nnnnnnnnnn nnnnnnnnnn nnnnnnnnnn nnnnnnnnnn 10740
nnnnnnnnnn nnnnnnnnnn nnnnnnnnnn nnnnnnnnnn nnnnnnnnnn nnnnnnnnnn 10800
nnnnnnnnnn nnnnnnnnnn nnnnnnnnnn nnnnnnnnnn nnnnnnnnnn nnnnnnnnnn 10860
nnnnnnnnnn nnnnnnnnnn nnnnnnnnnn nnnnnnnnnn nnnnnnnnnn nnnnnnnnnn 10920
nnnnnnnnnn nnnnnnnnnn nnnnnnnnnn nnnnnnnnnn nnnnnnnnnn nnnnnnnnnn 10980
nnnnnnnnnn nnnnnnnnnn nnnnnnnnnn nnnnnnnnnn nnnnnnnnnn nnnnnnnnnn 11040
nnnnnnnnnn nnnnnnnnnn nnnnnnnnnn nnnnnnnnnn nnnnnnnnnn nnnnnnnnnn 11100
nnnnnnnnnn nnnnnnnnnn nnnnnnnnnn nnnnnnnnnn nnnnnnnnnn nnnnnnnnnn 11160
nnnnnnnnnn nnnnnnnnnn nnnnnnnnnn nnnnnnnnnn nnnnnnnnnn nnnnnnnnnn 11220
nnnnnnnnnn nnnnnnnnnn nnnnnnnnnn nnnnnnnnnn nnnnnnnnnn nnnnnnnnnn 11280
nnnnnnnnnn nnnnnnnnnn nnnnnnnnnn nnnnnnnnnn nnnnnnnnnn nnnnnnnnnn 11340
nnnnnnnnnn nnnnnnnnnn nnnnnnnnnn nnnnnnnnnn nnnnnnnnnn nnnnnnnnnn 11400
nnnnnnnnnn nnnnnnnnnn nnnnnnnnnn nnnnnnnnnn nnnnnnnnnn nnnnnnnnnn 11460
nnnnnnnnnn nnnnnnnnnn nnnnnnnnnn nnnnnnnnnn nnnnnnnnnn nnnnnnnnnn 11520
nnnnnnnnnn nnnnnnnnnn nnnnnnnnnn nnnnnnnnnn nnnnnnnnnn nnnnnnnnnn 11580
nnnnnnnnnn nnnnnnnnnn nnnnnnnnnn nnnnnnnnnn nnnnnnnnnn nnnnnnnnnn 11640
nnnnnnnnnn nnnnnnnnnn nnnnnnnnnn nnnnnnnnnn nnnnnnnnnn nnnnnnnnnn 11700
nnnnnnnnnn nnnnnnnnnn nnnnnnnnnn nnnnnnnnnn nnnnnnnnnn nnnnnnnnnn 11760
nnnnnnnnnn nnnnnnnnnn nnnnnnnnnn nnnnnnnnnn nnnnnnnnnn nnnnnnnnnn 11820
nnnnnnnnnn nnnnnnnnnn nnnnnnnnnn nnnnnnnnnn nnnnnnnnnn nnnnnnnnnn 11880
nnnnnnnnnn nnnnnnnnnn nnnnnnnnnn nnnnnnnnnn nnnnnnnnnn nnnnnnnnnn 11940
nnnnnnnnnn nnnnnnnnnn nnnnnnnnnn nnnnnnnnnn nnnnnnnnnn nnnnnnnnnn 12000
nnnnnnnnnn nnnnnnnnnn nnnnnnnnnn nnnnnnnnnn nnnnnnnnnn nnnnnnnnnn 12060
nnnnnnnnnn nnnnnnnnnn nnnnnnnnnn nnnnnnnnnn nnnnnnnnnn nnnnnnnnnn 12120
nnnnnnnnnn nnnnnnnnnn nnnnnnnnnn nnnnnnnnnn nnnnnnnnnn nnnnnnnnnn 12180
nnnnnnnnnn nnnnnnnnnn nnnnnnnnnn nnnnnnnnnn nnnnnnnnnn nnnnnnnnnn 12240
nnnnnnnnnn nnnnnnnnnn nnnnnnnnnn nnnnnnnnnn nnnnnnnnnn nnnnnnnnnn 12300
nnnnnnnnnn nnnnnnnnnn nnnnnnnnnn nnnnnnnnnn nnnnnnnnnn nnnnnnnnnn 12360
nnnnnnnnnn nnnnnnnnnn nnnnnnnnnn nnnnnnnnnn nnnnnnnnnn nnnnnnnnnn 12420
nnnnnnnnnn nnnnnnnnnn nnnnnnnnnn nnnnnnnnnn nnnnnnnnnn nnnnnnnnnn 12480
nnnnnnnnnn nnnnnnnnnn nnnnnnnnnn nnnnnnnnnn nnnnnnnnnn nnnnnnnnnn 12540

-continued

```
nnnnnnnnnn nnnnnnnnnn nnnnnnnnnn nnnnnnnnnn nnnnnnnnnn nnnnnnnnnn  12600
nnnnnnnnnn nnnnnnnnnn nnnnnnnnnn nnnnnnnnnn nnnnnnnnnn nnnnnnnnnn  12660
nnnnnnnnnn nnnnnnnnnn nnnnnnnnnn nnnnnnnnnn nnnnnnnnnn nnnnnnnnnn  12720
nnnnnnnnnn nnnnnnnnnn nnnnnnnnnn nnnnnnnnnn nnnnnnnnnn nnnnnnnnnn  12780
nnnnnnnnnn nnnnnnnnnn nnnnnnnnnn nnnnnnnnnn nnnnnnnnnn nnnnnnnnnn  12840
nnnnnnnnnn nnnnnnnnnn nnnnnnnnnn nnnnnnnnnn nnnnnnnnnn nnnnnnnnnn  12900
nnnnnnnnnn nnnnnnnnnn nnnnnnnnnn nnnnnnnnnn nnnnnnnnnn nnnnnnnnnn  12960
nnnnnnnnnn nnnnnnnnnn nnnnnnnnnn nnnnnnnnnn nnnnnnnnnn nnnnnnnnnn  13020
nnnnnnnnnn nnnnnnnnnn nnnnnnnnnn nnnnnnnnnn nnnnnnnnnn nnnnnnnnnn  13080
nnnnnnnnnn nnnnnnnnnn nnnnnnnnnn nnnnnnnnnn nnnnnnnnnn nnnnnnnnnn  13140
nnnnnnnnnn nnnnnnnnnn nnnnnnnnnn nnnnnnnnnn nnnnnnnnnn nnnnnnnnnn  13200
nnnnnnnnnn nnnnnnnnnn nnnnnnnnnn nnnnnnnnnn nnnnnnnnnn nnnnnnnnnn  13260
nnnnnnnnnn nnnnnnnnnn nnnnnnnnnn nnnnnnnnnn nnnnnnnnnn nnnnnnnnnn  13320
nnnnnnnnnn nnnnnnnnnn nnnnnnnnnn nnnnnnnnnn nnnnnnnnnn nnnnnnnnnn  13380
nnnnnnnnnn nnnnnnnnnn nnnnnnnnnn nnnnnnnnnn nnnnnnnnnn nnnnnnnnnn  13440
nnnnnnnnnn nnnnnnnnnn nnnnnnnnnn nnnnnnnnnn nnnnnnnnnn nnnnnnnnnn  13500
nnnnnnnnnn nnnnnnnnnn nnnnnnnnnn nnnnnnnnnn nnnnnnnnnn nnnnnnnnnn  13560
nnnnnnnnnn nnnnnnnnnn nnnnnnnnnn nnnnnnnnnn nnnnnnnnnn nnnnnnnnnn  13620
nnnnnnnnnn nnnnnnnnnn nnnnnnnnnn nnnnnnnnnn nnnnnnnnnn nnnnnnnnnn  13680
nnnnnnnnnn nnnnnnnnnn nnnnnnnnnn nnnnnnnnnn nnnnnnnnnn nnnnnnnnnn  13740
nnnnnnnnnn nnnnnnnnnn nnnnnnnnnn nnnnnnnnnn nnnnnnnnnn nnnnnnnnnn  13800
nnnnnnnnnn nnnnnnnnnn nnnnnnnnnn nnnnnnnnnn nnnnnnnnnn nnnnnnnnnn  13860
nnnnnnnnnn nnnnnnnnnn nnnnnnnnnn nnnnnnnnnn nnnnnnnnnn nnnnnnnnnn  13920
nnnnnnnnnn nnnnnnnnnn nnnnnnnnnn nnnnnnnnnn nnnnnnnnnn nnnnnnnnnn  13980
nnnnnnnnnn nnnnnnnnnn nnnnnnnnnn nnnnnnnnnn nnnnnnnnnn nnnnnnnnnn  14040
nnnnnnnnnn nnnnnnnnnn nnnnnnnnnn nnnnnnnnnn nnnnnnnnnn nnnnnnnnnn  14100
nnnnnnnnnn nnnnnnnnnn nnnnnnnnnn nnnnnnnnnn nnnnnnnnnn nnnnnnnnnn  14160
nnnnnnnnnn nnnnnnnnnn nnnnnnnnnn nnnnnnnnnn nnnnnnnnnn nnnnnnnnnn  14220
nnnnnnnnnn nnnnnnnnnn nnnnnnnnnn nnnnnnnnnn nnnnnnnnnn nnnnnnnnnn  14280
nnnnnnnnnn nnnnnnnnnn nnnnnnnnnn nnnnnnnnnn nnnnnnnnnn nnnnnnnnnn  14340
nnnnnnnnnn nnnnnnnnnn nnnnnnnnnn nnnnnnnnnn nnnnnnnnnn nnnnnnnnnn  14400
nnnnnnnnnn nnnnnnnnnn nnnnnnnnnn nnnnnnnnnn nnnnnnnnnn nnnnnnnnnn  14460
nnnnnnnnnn nnnnnnnnnn nnnnnnnnnn nnnnnnnnnn nnnnnnnnnn nnnnnnnnnn  14520
nnnnnnnnnn nnnnnnnnnn nnnnnnnnnn nnnnnnnnnn nnnnnnnnnn nnnnnnnnnn  14580
nnnnnnnnnn nnnnnnnnnn nnnnnnnnnn nnnnnnnnnn nnnnnnnnnn nnnnnnnnnn  14640
nnnnnnnnnn nnnnnnnnnn nnnnnnnnnn nnnnnnnnnn nnnnnnnnnn nnnnnnnnnn  14700
nnnnnnnnnn nnnnnnnnnn nnnnnnnnnn nnnnnnnnnn nnnnnnnnnn nnnnnnnnnn  14760
nnnnnnnnnn nnnnnnnnnn nnnnnnnnnn nnnnnnnnnn nnnnnnnnnn nnnnnnnnnn  14820
nnnnnnnnnn nnnnnnnnnn nnnnnnnnnn nnnnnnnnnn nnnnnnnnnn nnnnnnnnnn  14880
nnnnnnnnnn nnnnnnnnnn nnnnnnnnnn nnnnnnnnnn nnnnnnnnnn nnnnnnnnnn  14940
```

-continued nnnnnnnnnn nnnnnnnnnn nnnnnnnnnn nnnnnnnnnn nnnnnnnnnn nnnnnnnnnn 15000
nnnnnnnnnn nnnnnnnnnn nnnnnnnnnn nnnnnnnnnn nnnnnnnnnn nnnnnnnnnn 15060
nnnnnnnnnn nnnnnnnnnn nnnnnnnnnn nnnnnnnnnn nnnnnnnnnn nnnnnnnnnn 15120
nnnnnnnnnn nnnnnnnnnn nnnnnnnnnn nnnnnnnnnn nnnnnnnnnn nnnnnnnnnn 15180
nnnnnnnnnn nnnnnnnnnn nnnnnnnnnn nnnnnnnnnn nnnnnnnnnn nnnnnnnnnn 15240
nnnnnnnnnn nnnnnnnnnn nnnnnnnnnn nnnnnnnnnn nnnnnnnnnn nnnnnnnnnn 15300
nnnnnnnnnn nnnnnnnnnn nnnnnnnnnn nnnnnnnnnn nnnnnnnnnn nnnnnnnnnn 15360
nnnnnnnnnn nnnnnnnnnn nnnnnnnnnn nnnnnnnnnn nnnnnnnnnn nnnnnnnnnn 15420
nnnnnnnnnn nnnnnnnnnn nnnnnnnnnn nnnnnnnnnn nnnnnnnnnn nnnnnnnnnn 15480
nnnnnnnnnn nnnnnnnnnn nnnnnnnnnn nnnnnnnnnn nnnnnnnnnn nnnnnnnnnn 15540
nnnnnnnnnn nnnnnnnnnn nnnnnnnnnn nnnnnnnnnn nnnnnnnnnn nnnnnnnnnn 15600
nnnnnnnnnn nnnnnnnnnn nnnnnnnnnn nnnnnnnnnn nnnnnnnnnn nnnnnnnnnn 15660
nnnnnnnnnn nnnnnnnnnn nnnnnnnnnn nnnnnnnnnn nnnnnnnnnn nnnnnnnnnn 15720
nnnnnnnnnn nnnnnnnnnn nnnnnnnnnn nnnnnnnnnn nnnnnnnnnn nnnnnnnnnn 15780
nnnnnnnnnn nnnnnnnnnn nnnnnnnnnn nnnnnnnnnn nnnnnnnnnn nnnnnnnnnn 15840
nnnnnnnnnn nnnnnnnnnn nnnnnnnnnn nnnnnnnnnn nnnnnnnnnn nnnnnnnnnn 15900
nnnnnnnnnn nnnnnnnnnn nnnnnnnnnn nnnnnnnnnn nnnnnnnnnn nnnnnnnnnn 15960
nnnnnnnnnn nnnnnnnnnn nnnnnnnnnn nnnnnnnnnn nnnnnnnnnn nnnnnnnnnn 16020
nnnnnnnnnn nnnnnnnnnn nnnnnnnnnn nnnnnnnnnn nnnnnnnnnn nnnnnnnnnn 16080
nnnnnnnnnn nnnnnnnnnn nnnnnnnnnn nnnnnnnnnn nnnnnnnnnn nnnnnnnnnn 16140
nnnnnnnnnn nnnnnnnnnn nnnnnnnnnn nnnnnnnnnn nnnnnnnnnn nnnnnnnnnn 16200
nnnnnnnnnn nnnnnnnnnn nnnnnnnnnn nnnnnnnnnn nnnnnnnnnn nnnnnnnnnn 16260
nnnnnnnnnn nnnnnnnnnn nnnnnnnnnn nnnnnnnnnn nnnnnnnnnn nnnnnnnnnn 16320
nnnnnnnnnn nnnnnnnnnn nnnnnnnnnn nnnnnnnnnn nnnnnnnnnn nnnnnnnnnn 16380
nnnnnnnnnn nnnnnnnnnn nnnnnnnnnn nnnnnnnnnn nnnnnnnnnn nnnnnnnnnn 16440
nnnnnnnnnn nnnnnnnnnn nnnnnnnnnn nnnnnnnnnn nnnnnnnnnn nnnnnnnnnn 16500
nnnnnnnnnn nnnnnnnnnn nnnnnnnnnn nnnnnnnnnn nnnnnnnnnn nnnnnnnnnn 16560
nnnnnnnnnn nnnnnnnnnn nnnnnnnnnn nnnnnnnnnn nnnnnnnnnn nnnnnnnnnn 16620
nnnnnnnnnn nnnnnnnnnn nnnnnnnnnn nnnnnnnnnn nnnnnnnnnn nnnnnnnnnn 16680
nnnnnnnnnn nnnnnnnnnn nnnnnnnnnn nnnnnnnnnn nnnnnnnnnn nnnnnnnnnn 16740
nnnnnnnnnn nnnnnnnnnn nnnnnnnnnn nnnnnnnnnn nnnnnnnnnn nnnnnnnnnn 16800
nnnnnnnnnn nnnnnnnnnn nnnnnnnnnn nnnnnnnnnn nnnnnnnnnn nnnnnnnnnn 16860
nnnnnnnnnn nnnnnnnnnn nnnnnnnnnn nnnnnnnnnn nnnnnnnnnn nnnnnnnnnn 16920
nnnnnnnnnn nnnnnnnnnn nnnnnnnnnn nnnnnnnnnn nnnnnnnnnn nnnnnnnnnn 16980
nnnnnnnnnn nnnnnnnnnn nnnnnnnnnn nnnnnnnnnn nnnnnnnnnn nnnnnnnnnn 17040
nnnnnnnnnn nnnnnnnnnn nnnnnnnnnn nnnnnnnnnn nnnnnnnnnn nnnnnnnnnn 17100
nnnnnnnnnn nnnnnnnnnn nnnnnnnnnn nnnnnnnnnn nnnnnnnnnn nnnnnnnnnn 17160
nnnnnnnnnn nnnnnnnnnn nnnnnnnnnn nnnnnnnnnn nnnnnnnnnn nnnnnnnnnn 17220
nnnnnnnnnn nnnnnnnnnn nnnnnnnnnn nnnnnnnnnn nnnnnnnnnn nnnnnnnnnn 17280

-continued

```
nnnnnnnnnn nnnnnnnnnn nnnnnnnnnn nnnnnnnnnn nnnnnnnnnn nnnnnnnnnn  17340
nnnnnnnnnn nnnnnnnnnn nnnnnnnnnn nnnnnnnnnn nnnnnnnnnn nnnnnnnnnn  17400
nnnnnnnnnn nnnnnnnnnn nnnnnnnnnn nnnnnnnnnn nnnnnnnnnn nnnnnnnnnn  17460
nnnnnnnnnn nnnnnnnnnn nnnnnnnnnn nnnnnnnnnn nnnnnnnnnn nnnnnnnnnn  17520
nnnnnnnnnn nnnnnnnnnn nnnnnnnnnn nnnnnnnnnn nnnnnnnnnn nnnnnnnnnn  17580
nnnnnnnnnn nnnnnnnnnn nnnnnnnnnn nnnnnnnnnn nnnnnnnnnn nnnnnnnnnn  17640
nnnnnnnnnn nnnnnnnnnn nnnnnnnnnn nnnnnnnnnn nnnnnnnnnn nnnnnnnnnn  17700
nnnnnnnnnn nnnnnnnnnn nnnnnnnnnn nnnnnnnnnn nnnnnnnnnn nnnnnnnnnn  17760
nnnnnnnnnn nnnnnnnnnn nnnnnnnnnn nnnnnnnnnn nnnnnnnnnn nnnnnnnnnn  17820
nnnnnnnnnn nnnnnnnnnn nnnnnnnnnn nnnnnnnnnn nnnnnnnnnn nnnnnnnnnn  17880
nnnnnnnnnn nnnnnnnnnn nnnnnnnnnn nnnnnnnnnn nnnnnnnnnn nnnnnnnnnn  17940
nnnnnnnnnn nnnnnnnnnn nnnnnnnnnn nnnnnnnnnn nnnnnnnnnn nnnnnnnnnn  18000
nnnnnnnnnn nnnnnnnnnn nnnnnnnnnn nnnnnnnnnn nnnnnnnnnn nnnnnnnnnn  18060
nnnnnnnnnn nnnnnnnnnn nnnnnnnnnn nnnnnnnnnn nnnnnnnnnn nnnnnnnnnn  18120
nnnnnnnnnn nnnnnnnnnn nnnnnnnnnn nnnnnnnnnn nnnnnnnnnn nnnnnnnnnn  18180
nnnnnnnnnn nnnnnnnnnn nnnnnnnnnn nnnnnnnnnn nnnnnnnnnn nnnnnnnnnn  18240
nnnnnnnnnn nnnnnnnnnn nnnnnnnnnn nnnnnnnnnn nnnnnnnnnn nnnnnnnnnn  18300
nnnnnnnnnn nnnnnnnnnn nnnnnnnnnn nnnnnnnnnn nnnnnnnnnn nnnnnnnnnn  18360
nnnnnnnnnn nnnnnnnnnn nnnnnnnnnn nnnnnnnnnn nnnnnnnnnn nnnnnnnnnn  18420
nnnnnnnnnn nnnnnnnnnn nnnnnnnnnn nnnnnnnnnn nnnnnnnnnn nnnnnnnnnn  18480
nnnnnnnnnn nnnnnnnnnn nnnnnnnnnn nnnnnnnnnn nnnnnnnnnn nnnnnnnnnn  18540
nnnnnnnnnn nnnnnnnnnn nnnnnnnnnn nnnnnnnnnn nnnnnnnnnn nnnnnnnnnn  18600
nnnnnnnnnn nnnnnnnnnn nnnnnnnnnn nnnnnnnnnn nnnnnnnnnn nnnnnnnnnn  18660
nnnnnnnnnn nnnnnnnnnn nnnnnnnnnn nnnnnnnnnn nnnnnnnnnn nnnnnnnnnn  18720
nnnnnnnnnn nnnnnnnnnn nnnnnnnnnn nnnnnnnnnn nnnnnnnnnn nnnnnnnnnn  18780
nnnnnnnnnn nnnnnnnnnn nnnnnnnnnn nnnnnnnnnn nnnnnnnnnn nnnnnnnnnn  18840
nnnnnnnnnn nnnnnnnnnn nnnnnnnnnn nnnnnnnnnn nnnnnnnnnn nnnnnnnnnn  18900
nnnnnnnnnn nnnnnnnnnn nnnnnnnnnn nnnnnnnnnn nnnnnnnnnn nnnnnnnnnn  18960
nnnnnnnnnn nnnnnnnnnn nnnnnnnnnn nnnnnnnnnn nnnnnnnnnn nnnnnnnnnn  19020
nnnnnnnnnn nnnnnnnnnn nnnnnnnnnn nnnnnnnnnn nnnnnnnnnn nnnnnnnnnn  19080
nnnnnnnnnn nnnnnnnnnn nnnnnnnnnn nnnnnnnnnn nnnnnnnnnn nnnnnnnnnn  19140
nnnnnnnnnn nnnnnnnnnn nnnnnnnnnn nnnnnnnnnn nnnnnnnnnn nnnnnnnnnn  19200
nnnnnnnnnn nnnnnnnnnn nnnnnnnnnn nnnnnnnnnn nnnnnnnnnn nnnnnnnnnn  19260
nnnnnnnnnn nnnnnnnnnn nnnnnnnnnn nnnnnnnnnn nnnnnnnnnn nnnnnnnnnn  19320
nnnnnnnnnn nnnnnnnnnn nnnnnnnnnn nnnnnnnnnn nnnnnnnnnn nnnnnnnnnn  19380
nnnnnnnnnn nnnnnnnnnn nnnnnnnnnn nnnnnnnnnn nnnnnnnnnn nnnnnnnnnn  19440
nnnnnnnnnn nnnnnnnnnn nnnnnnnnnn nnnnnnnnnn nnnnnnnnnn nnnnnnnnnn  19500
nnnnnnnnnn nnnnnnnnnn nnnnnnnnnn nnnnnnnnnn nnnnnnnnnn nnnnnnnnnn  19560
nnnnnnnnnn nnnnnnnnnn nnnnnnnnnn nnnnnnnnnn nnnnnnnnnn nnnnnnnnnn  19620
nnnnnnnnnn nnnnnnnnnn nnnnnnnnnn nnnnnnnnnn nnnnnnnnnn nnnnnnnnnn  19680
```

-continued

```
nnnnnnnnnn nnnnnnnnnn nnnnnnnnnn nnnnnnnnnn nnnnnnnnnn nnnnnnnnnn  19740
nnnnnnnnnn nnnnnnnnnn nnnnnnnnnn nnnnnnnnnn nnnnnnnnnn nnnnnnnnnn  19800
nnnnnnnnnn nnnnnnnnnn nnnnnnnnnn nnnnnnnnnn nnnnnnnnnn nnnnnnnnnn  19860
nnnnnnnnnn nnnnnnnnnn nnnnnnnnnn nnnnnnnnnn nnnnnnnnnn nnnnnnnnnn  19920
nnnnnnnnnn nnnnnnnnnn nnnnnnnnnn nnnnnnnnnn nnnnnnnnnn nnnnnnnnnn  19980
nnnnnnnnnn nnnnnnnnnn nnnnnnnnnn nnnnnnnnnn nnnnnnnnnn nnnnnnnnnn  20040
nnnnnnnnnn nnnnnnnnnn nnnnnnnnnn nnnnnnnnnn nnnnnnnnnn nnnnnnnnnn  20100
nnnnnnnnnn nnnnnnnnnn nnnnnnnnnn nnnnnnnnnn nnnnnnnnnn nnnnnnnnnn  20160
nnnnnnnnnn nnnnnnnnnn nnnnnnnnnn nnnnnnnnnn nnnnnnnnnn nnnnnnnnnn  20220
nnnnnnnnnn nnnnnnnnnn nnnnnnnnnn nnnnnnnnnn nnnnnnnnnn nnnnnnnnnn  20280
nnnnnnnnnn nnnnnnnnnn nnnnnnnnnn nnnnnnnnnn nnnnnnnnnn nnnnnnnnnn  20340
nnnnnnnnnn nnnnnnnnnn nnnnnnnnnn nnnnnnnnnn nnnnnnnnnn nnnnnnnnnn  20400
nnnnnnnnnn nnnnnnnnnn nnnnnnnnnn nnnnnnnnnn nnnnnnnnnn nnnnnnnnnn  20460
nnnnnnnnnn nnnnnnnnnn nnnnnnnnnn nnnnnnnnnn nnnnnnnnnn nnnnnnnnnn  20520
nnnnnnnnnn nnnnnnnnnn nnnnnnnnnn nnnnnnnnnn nnnnnnnnnn nnnnnnnnnn  20580
nnnnnnnnnn nnnnnnnnnn nnnnnnnnnn nnnnnnnnnn nnnnnnnnnn nnnnnnnnnn  20640
nnnnnnnnnn nnnnnnnnnn nnnnnnnnnn nnnnnnnnnn nnnnnnnnnn nnnnnnnnnn  20700
nnnnnnnnnn nnnnnnnnnn nnnnnnnnnn nnnnnnnnnn nnnnnnnnnn nnnnnnnnnn  20760
nnnnnnnnnn nnnnnnnnnn nnnnnnnnnn nnnnnnnnnn nnnnnnnnnn nnnnnnnnnn  20820
nnnnnnnnnn nnnnnnnnnn nnnnnnnnnn nnnnnnnnnn nnnnnnnnnn nnnnnnnnnn  20880
nnnnnnnnnn nnnnnnnnnn nnnnnnnnnn nnnnnnnnnn nnnnnnnnnn nnnnnnnnnn  20940
nnnnnnnnnn nnnnnnnnnn nnnnnnnnnn nnnnnnnnnn nnnnnnnnnn nnnnnnnnnn  21000
nnnnnnnnnn nnnnnnnnnn nnnnnnnnnn nnnnnnnnnn nnnnnnnnnn nnnnnnnnnn  21060
nnnnnnnnnn nnnnnnnnnn nnnnnnnnnn nnnnnnnnnn nnnnnnnnnn nnnnnnnnnn  21120
nnnnnnnnnn nnnnnnnnnn nnnnnnnnnn nnnnnnnnnn nnnnnnnnnn nnnnnnnnnn  21180
nnnnnnnnnn nnnnnnnnnn nnnnnnnnnn nnnnnnnnnn nnnnnnnnnn nnnnnnnnnn  21240
nnnnnnnnnn nnnnnnnnnn nnnnnnnnnn nnnnnnnnnn nnnnnnnnnn nnnnnnnnnn  21300
nnnnnnnnnn nnnnnnnnnn nnnnnnnnnn nnnnnnnnnn nnnnnnnnnn nnnnnnnnnn  21360
nnnnnnnnnn nnnnnnnnnn nnnnnnnnnn nnnnnnnnnn nnnnnnnnnn nnnnnnnnnn  21420
nnnnnnnnnn nnnnnnnnnn nnnnnnnnnn nnnnnnnnnn nnnnnnnnnn nnnnnnnnnn  21480
nnnnnnnnnn nnnnnnnnnn nnnnnnnnnn nnnnnnnnnn nnnnnnnnnn nnnnnnnnnn  21540
nnnnnnnnnn nnnnnnnnnn nnnnnnnnnn nnnnnnnnnn nnnnnnnnnn nnnnnnnnnn  21600
nnnnnnnnnn nnnnnnnnnn nnnnnnnnnn nnnnnnnnnn nnnnnnnnnn nnnnnnnnnn  21660
nnnnnnnnnn nnnnnnnnnn nnnnnnnnnn nnnnnnnnnn nnnnnnnnnn nnnnnnnnnn  21720
nnnnnnnnnn nnnnnnnnnn nnnnnnnnnn nnnnnnnnnn nnnnnnnnnn nnnnnnnnnn  21780
nnnnnnnnnn nnnnnnnnnn nnnnnnnnnn nnnnnnnnnn nnnnnnnnnn nnnnnnnnnn  21840
nnnnnnnnnn nnnnnnnnnn nnnnnnnnnn nnnnnnnnnn nnnnnnnnnn nnnnnnnnnn  21900
nnnnnnnnnn nnnnnnnnnn nnnnnnnnnn nnnnnnnnnn nnnnnnnnnn nnnnnnnnnn  21960
nnnnnnnnnn nnnnnnnnnn nnnnnnnnnn nnnnnnnnnn nnnnnnnnnn nnnnnnnnnn  22020
```

-continued nnnnnnnnnn nnnnnnnnnn nnnnnnnnnn nnnnnnnnnn nnnnnnnnnn nnnnnnnnnn 22080
nnnnnnnnnn nnnnnnnnnn nnnnnnnnnn nnnnnnnnnn nnnnnnnnnn nnnnnnnnnn 22140
nnnnnnnnnn nnnnnnnnnn nnnnnnnnnn nnnnnnnnnn nnnnnnnnnn nnnnnnnnnn 22200
nnnnnnnnnn nnnnnnnnnn nnnnnnnnnn nnnnnnnnnn nnnnnnnnnn nnnnnnnnnn 22260
nnnnnnnnnn nnnnnnnnnn nnnnnnnnnn nnnnnnnnnn nnnnnnnnnn nnnnnnnnnn 22320
nnnnnnnnnn nnnnnnnnnn nnnnnnnnnn nnnnnnnnnn nnnnnnnnnn nnnnnnnnnn 22380
nnnnnnnnnn nnnnnnnnnn nnnnnnnnnn nnnnnnnnnn nnnnnnnnnn nnnnnnnnnn 22440
nnnnnnnnnn nnnnnnnnnn nnnnnnnnnn nnnnnnnnnn nnnnnnnnnn nnnnnnnnnn 22500
nnnnnnnnnn nnnnnnnnnn nnnnnnnnnn nnnnnnnnnn nnnnnnnnnn nnnnnnnnnn 22560
nnnnnnnnnn nnnnnnnnnn nnnnnnnnnn nnnnnnnnnn nnnnnnnnnn nnnnnnnnnn 22620
nnnnnnnnnn nnnnnnnnnn nnnnnnnnnn nnnnnnnnnn nnnnnnnnnn nnnnnnnnnn 22680
nnnnnnnnnn nnnnnnnnnn nnnnnnnnnn nnnnnnnnnn nnnnnnnnnn nnnnnnnnnn 22740
nnnnnnnnnn nnnnnnnnnn nnnnnnnnnn nnnnnnnnnn nnnnnnnnnn nnnnnnnnnn 22800
nnnnnnnnnn nnnnnnnnnn nnnnnnnnnn nnnnnnnnnn nnnnnnnnnn nnnnnnnnnn 22860
nnnnnnnnnn nnnnnnnnnn nnnnnnnnnn nnnnnnnnnn nnnnnnnnnn nnnnnnnnnn 22920
nnnnnnnnnn nnnnnnnnnn nnnnnnnnnn nnnnnnnnnn nnnnnnnnnn nnnnnnnnnn 22980
nnnnnnnnnn nnnnnnnnnn nnnnnnnnnn nnnnnnnnnn nnnnnnnnnn nnnnnnnnnn 23040
nnnnnnnnnn nnnnnnnnnn nnnnnnnnnn nnnnnnnnnn nnnnnnnnnn nnnnnnnnnn 23100
nnnnnnnnnn nnnnnnnnnn nnnnnnnnnn nnnnnnnnnn nnnnnnnnnn nnnnnnnnnn 23160
nnnnnnnnnn nnnnnnnnnn nnnnnnnnnn nnnnnnnnnn nnnnnnnnnn nnnnnnnnnn 23220
nnnnnnnnnn nnnnnnnnnn nnnnnnnnnn nnnnnnnnnn nnnnnnnnnn nnnnnnnnnn 23280
nnnnnnnnnn nnnnnnnnnn nnnnnnnnnn nnnnnnnnnn nnnnnnnnnn nnnnnnnnnn 23340
nnnnnnnnnn nnnnnnnnnn nnnnnnnnnn nnnnnnnnnn nnnnnnnnnn nnnnnnnnnn 23400
nnnnnnnnnn nnnnnnnnnn nnnnnnnnnn nnnnnnnnnn nnnnnnnnnn nnnnnnnnnn 23460
nnnnnnnnnn nnnnnnnnnn nnnnnnnnnn nnnnnnnnnn nnnnnnnnnn nnnnnnnnnn 23520
nnnnnnnnnn nnnnnnnnnn nnnnnnnnnn nnnnnnnnnn nnnnnnnnnn nnnnnnnnnn 23580
nnnnnnnnnn nnnnnnnnnn nnnnnnnnnn nnnnnnnnnn nnnnnnnnnn nnnnnnnnnn 23640
nnnnnnnnnn nnnnnnnnnn nnnnnnnnnn nnnnnnnnnn nnnnnnnnnn nnnnnnnnnn 23700
nnnnnnnnnn nnnnnnnnnn nnnnnnnnnn nnnnnnnnnn nnnnnnnnnn nnnnnnnnnn 23760
nnnnnnnnnn nnnnnnnnnn nnnnnnnnnn nnnnnnnnnn nnnnnnnnnn nnnnnnnnnn 23820
nnnnnnnnnn nnnnnnnnnn nnnnnnnnnn nnnnnnnnnn nnnnnnnnnn nnnnnnnnnn 23880
nnnnnnnnnn nnnnnnnnnn nnnnnnnnnn nnnnnnnnnn nnnnnnnnnn nnnnnnnnnn 23940
nnnnnnnnnn nnnnnnnnnn nnnnnnnnnn nnnnnnnnnn nnnnnnnnnn nnnnnnnnnn 24000
nnnnnnnnnn nnnnnnnnnn nnnnnnnnnn nnnnnnnnnn nnnnnnnnnn nnnnnnnnnn 24060
nnnnnnnnnn nnnnnnnnnn nnnnnnnnnn nnnnnnnnnn nnnnnnnnnn nnnnnnnnnn 24120
nnnnnnnnnn nnnnnnnnnn nnnnnnnnnn nnnnnnnnnn nnnnnnnnnn nnnnnnnnnn 24180
nnnnnnnnnn nnnnnnnnnn nnnnnnnnnn nnnnnnnnnn nnnnnnnnnn nnnnnnnnnn 24240
nnnnnnnnnn nnnnnnnnnn nnnnnnnnnn nnnnnnnnnn nnnnnnnnnn nnnnnnnnnn 24300
nnnnnnnnnn nnnnnnnnnn nnnnnnnnnn nnnnnnnnnn nnnnnnnnnn nnnnnnnnnn 24360
nnnnnnnnnn nnnnnnnnnn nnnnnnnnnn nnnnnnnnnn nnnnnnnnnn nnnnnnnnnn 24420

-continued

```
nnnnnnnnnn nnnnnnnnnn nnnnnnnnnn nnnnnnnnnn nnnnnnnnnn nnnnnnnnnn  24480
nnnnnnnnnn nnnnnnnnnn nnnnnnnnnn nnnnnnnnnn nnnnnnnnnn nnnnnnnnnn  24540
nnnnnnnnnn nnnnnnnnnn nnnnnnnnnn nnnnnnnnnn nnnnnnnnnn nnnnnnnnnn  24600
nnnnnnnnnn nnnnnnnnnn nnnnnnnnnn nnnnnnnnnn nnnnnnnnnn nnnnnnnnnn  24660
nnnnnnnnnn nnnnnnnnnn nnnnnnnnnn nnnnnnnnnn nnnnnnnnnn nnnnnnnnnn  24720
nnnnnnnnnn nnnnnnnnnn nnnnnnnnnn nnnnnnnnnn nnnnnnnnnn nnnnnnnnnn  24780
nnnnnnnnnn nnnnnnnnnn nnnnnnnnnn nnnnnnnnnn nnnnnnnnnn nnnnnnnnnn  24840
nnnnnnnnnn nnnnnnnnnn nnnnnnnnnn nnnnnnnnnn nnnnnnnnnn nnnnnnnnnn  24900
nnnnnnnnnn nnnnnnnnnn nnnnnnnnnn nnnnnnnnnn nnnnnnnnnn nnnnnnnnnn  24960
nnnnnnnnnn nnnnnnnnnn nnnnnnnnnn nnnnnnnnnn nnnnnnnnnn nnnnnnnnnn  25020
nnnnnnnnnn nnnnnnnnnn nnnnnnnnnn nnnnnnnnnn nnnnnnnnnn nnnnnnnnnn  25080
nnnnnnnnnn nnnnnnnnnn nnnnnnnnnn nnnnnnnnnn nnnnnnnnnn nnnnnnnnnn  25140
nnnnnnnnnn nnnnnnnnnn nnnnnnnnnn nnnnnnnnnn nnnnnnnnnn nnnnnnnnnn  25200
nnnnnnnnnn nnnnnnnnnn nnnnnnnnnn nnnnnnnnnn nnnnnnnnnn nnnnnnnnnn  25260
nnnnnnnnnn nnnnnnnnnn nnnnnnnnnn nnnnnnnnnn nnnnnnnnnn nnnnnnnnnn  25320
nnnnnnnnnn nnnnnnnnnn nnnnnnnnnn nnnnnnnnnn nnnnnnnnnn nnnnnnnnnn  25380
nnnnnnnnnn nnnnnnnnnn nnnnnnnnnn nnnnnnnnnn nnnnnnnnnn nnnnnnnnnn  25440
nnnnnnnnnn nnnnnnnnnn nnnnnnnnnn nnnnnnnnnn nnnnnnnnnn nnnnnnnnnn  25500
nnnnnnnnnn nnnnnnnnnn nnnnnnnnnn nnnnnnnnnn nnnnnnnnnn nnnnnnnnnn  25560
nnnnnnnnnn nnnnnnnnnn nnnnnnnnnn nnnnnnnnnn nnnnnnnnnn nnnnnnnnnn  25620
nnnnnnnnnn nnnnnnnnnn nnnnnnnnnn nnnnnnnnnn nnnnnnnnnn nnnnnnnnnn  25680
nnnnnnnnnn nnnnnnnnnn nnnnnnnnnn nnnnnnnnnn nnnnnnnnnn nnnnnnnnnn  25740
nnnnnnnnnn nnnnnnnnnn nnnnnnnnnn nnnnnnnnnn nnnnnnnnnn nnnnnnnnnn  25800
nnnnnnnnnn nnnnnnnnnn nnnnnnnnnn nnnnnnnnnn nnnnnnnnnn nnnnnnnnnn  25860
nnnnnnnnnn nnnnnnnnnn nnnnnnnnnn nnnnnnnnnn nnnnnnnnnn nnnnnnnnnn  25920
nnnnnnnnnn nnnnnnnnnn nnnnnnnnnn nnnnnnnnnn nnnnnnnnnn nnnnnnnnnn  25980
nnnnnnnnnn nnnnnnnnnn nnnnnnnnnn nnnnnnnnnn nnnnnnnnnn nnnnnnnnnn  26040
nnnnnnnnnn nnnnnnnnnn nnnnnnnnnn nnnnnnnnnn nnnnnnnnnn nnnnnnnnnn  26100
nnnnnnnnnn nnnnnnnnnn nnnnnnnnnn nnnnnnnnnn nnnnnnnnnn nnnnnnnnnn  26160
nnnnnnnnnn nnnnnnnnnn nnnnnnnnnn nnnnnnnnnn nnnnnnnnnn nnnnnnnnnn  26220
nnnnnnnnnn nnnnnnnnnn nnnnnnnnnn nnnnnnnnnn nnnnnnnnnn nnnnnnnnnn  26280
nnnnnnnnnn nnnnnnnnnn nnnnnnnnnn nnnnnnnnnn nnnnnnnnnn nnnnnnnnnn  26340
nnnnnnnnnn nnnnnnnnnn nnnnnnnnnn nnnnnnnnnn nnnnnnnnnn nnnnnnnnnn  26400
nnnnnnnnnn nnnnnnnnnn nnnnnnnnnn nnnnnnnnnn nnnnnnnnnn nnnnnnnnnn  26460
nnnnnnnnnn nnnnnnnnnn nnnnnnnnnn nnnnnnnnnn nnnnnnnnnn nnnnnnnnnn  26520
nnnnnnnnnn nnnnnnnnnn nnnnnnnnnn nnnnnnnnnn nnnnnnnnnn nnnnnnnnnn  26580
nnnnnnnnnn nnnnnnnnnn nnnnnnnnnn nnnnnnnnnn nnnnnnnnnn nnnnnnnnnn  26640
nnnnnnnnnn nnnnnnnnnn nnnnnnnnnn nnnnnnnnnn nnnnnnnnnn nnnnnnnnnn  26700
nnnnnnnnnn nnnnnnnnnn nnnnnnnnnn nnnnnnnnnn nnnnnnnnnn nnnnnnnnnn  26760
```

-continued nnnnnnnnnn nnnnnnnnnn nnnnnnnnnn nnnnnnnnnn nnnnnnnnnn nnnnnnnnnn 26820
nnnnnnnnnn nnnnnnnnnn nnnnnnnnnn nnnnnnnnnn nnnnnnnnnn nnnnnnnnnn 26880
nnnnnnnnnn nnnnnnnnnn nnnnnnnnnn nnnnnnnnnn nnnnnnnnnn nnnnnnnnnn 26940
nnnnnnnnnn nnnnnnnnnn nnnnnnnnnn nnnnnnnnnn nnnnnnnnnn nnnnnnnnnn 27000
nnnnnnnnnn nnnnnnnnnn nnnnnnnnnn nnnnnnnnnn nnnnnnnnnn nnnnnnnnnn 27060
nnnnnnnnnn nnnnnnnnnn nnnnnnnnnn nnnnnnnnnn nnnnnnnnnn nnnnnnnnnn 27120
nnnnnnnnnn nnnnnnnnnn nnnnnnnnnn nnnnnnnnnn nnnnnnnnnn nnnnnnnnnn 27180
nnnnnnnnnn nnnnnnnnnn nnnnnnnnnn nnnnnnnnnn nnnnnnnnnn nnnnnnnnnn 27240
nnnnnnnnnn nnnnnnnnnn nnnnnnnnnn nnnnnnnnnn nnnnnnnnnn nnnnnnnnnn 27300
nnnnnnnnnn nnnnnnnnnn nnnnnnnnnn nnnnnnnnnn nnnnnnnnnn nnnnnnnnnn 27360
nnnnnnnnnn nnnnnnnnnn nnnnnnnnnn nnnnnnnnnn nnnnnnnnnn nnnnnnnnnn 27420
nnnnnnnnnn nnnnnnnnnn nnnnnnnnnn nnnnnnnnnn nnnnnnnnnn nnnnnnnnnn 27480
nnnnnnnnnn nnnnnnnnnn nnnnnnnnnn nnnnnnnnnn nnnnnnnnnn nnnnnnnnnn 27540
nnnnnnnnnn nnnnnnnnnn nnnnnnnnnn nnnnnnnnnn nnnnnnnnnn nnnnnnnnnn 27600
nnnnnnnnnn nnnnnnnnnn nnnnnnnnnn nnnnnnnnnn nnnnnnnnnn nnnnnnnnnn 27660
nnnnnnnnnn nnnnnnnnnn nnnnnnnnnn nnnnnnnnnn nnnnnnnnnn nnnnnnnnnn 27720
nnnnnnnnnn nnnnnnnnnn nnnnnnnnnn nnnnnnnnnn nnnnnnnnnn nnnnnnnnnn 27780
nnnnnnnnnn nnnnnnnnnn nnnnnnnnnn nnnnnnnnnn nnnnnnnnnn nnnnnnnnnn 27840
nnnnnnnnnn nnnnnnnnnn nnnnnnnnnn nnnnnnnnnn nnnnnnnnnn nnnnnnnnnn 27900
nnnnnnnnnn nnnnnnnnnn nnnnnnnnnn nnnnnnnnnn nnnnnnnnnn nnnnnnnnnn 27960
nnnnnnnnnn nnnnnnnnnn nnnnnnnnnn nnnnnnnnnn nnnnnnnnnn nnnnnnnnnn 28020
nnnnnnnnnn nnnnnnnnnn nnnnnnnnnn nnnnnnnnnn nnnnnnnnnn nnnnnnnnnn 28080
nnnnnnnnnn nnnnnnnnnn nnnnnnnnnn nnnnnnnnnn nnnnnnnnnn nnnnnnnnnn 28140
nnnnnnnnnn nnnnnnnnnn nnnnnnnnnn nnnnnnnnnn nnnnnnnnnn nnnnnnnnnn 28200
nnnnnnnnnn nnnnnnnnnn nnnnnnnnnn nnnnnnnnnn nnnnnnnnnn nnnnnnnnnn 28260
nnnnnnnnnn nnnnnnnnnn nnnnnnnnnn nnnnnnnnnn nnnnnnnnnn nnnnnnnnnn 28320
nnnnnnnnnn nnnnnnnnnn nnnnnnnnnn nnnnnnnnnn nnnnnnnnnn nnnnnnnnnn 28380
nnnnnnnnnn nnnnnnnnnn nnnnnnnnnn nnnnnnnnnn nnnnnnnnnn nnnnnnnnnn 28440
nnnnnnnnnn nnnnnnnnnn nnnnnnnnnn nnnnnnnnnn nnnnnnnnnn nnnnnnnnnn 28500
nnnnnnnnnn nnnnnnnnnn nnnnnnnnnn nnnnnnnnnn nnnnnnnnnn nnnnnnnnnn 28560
nnnnnnnnnn nnnnnnnnnn nnnnnnnnnn nnnnnnnnnn nnnnnnnnnn nnnnnnnnnn 28620
nnnnnnnnnn nnnnnnnnnn nnnnnnnnnn nnnnnnnnnn nnnnnnnnnn nnnnnnnnnn 28680
nnnnnnnnnn nnnnnnnnnn nnnnnnnnnn nnnnnnnnnn nnnnnnnnnn nnnnnnnnnn 28740
nnnnnnnnnn nnnnnnnnnn nnnnnnnnnn nnnnnnnnnn nnnnnnnnnn nnnnnnnnnn 28800
nnnnnnnnnn nnnnnnnnnn nnnnnnnnnn nnnnnnnnnn nnnnnnnnnn nnnnnnnnnn 28860
nnnnnnnnnn nnnnnnnnnn nnnnnnnnnn nnnnnnnnnn nnnnnnnnnn nnnnnnnnnn 28920
nnnnnnnnnn nnnnnnnnnn nnnnnnnnnn nnnnnnnnnn nnnnnnnnnn nnnnnnnnnn 28980
nnnnnnnnnn nnnnnnnnnn nnnnnnnnnn nnnnnnnnnn nnnnnnnnnn nnnnnnnnnn 29040
nnnnnnnnnn nnnnnnnnnn nnnnnnnnnn nnnnnnnnnn nnnnnnnnnn nnnnnnnnnn 29100
nnnnnnnnnn nnnnnnnnnn nnnnnnnnnn nnnnnnnnnn nnnnnnnnnn nnnnnnnnnn 29160

-continued nnnnnnnnnn nnnnnnnnnn nnnnnnnnnn nnnnnnnnnn nnnnnnnnnn nnnnnnnnnn 29220
nnnnnnnnnn nnnnnnnnnn nnnnnnnnnn nnnnnnnnnn nnnnnnnnnn nnnnnnnnnn 29280
nnnnnnnnnn nnnnnnnnnn nnnnnnnnnn nnnnnnnnnn nnnnnnnnnn nnnnnnnnnn 29340
nnnnnnnnnn nnnnnnnnnn nnnnnnnnnn nnnnnnnnnn nnnnnnnnnn nnnnnnnnnn 29400
nnnnnnnnnn nnnnnnnnnn nnnnnnnnnn nnnnnnnnnn nnnnnnnnnn nnnnnnnnnn 29460
nnnnnnnnnn nnnnnnnnnn nnnnnnnnnn nnnnnnnnnn nnnnnnnnnn nnnnnnnnnn 29520
nnnnnnnnnn nnnnnnnnnn nnnnnnnnnn nnnnnnnnnn nnnnnnnnnn nnnnnnnnnn 29580
nnnnnnnnnn nnnnnnnnnn nnnnnnnnnn nnnnnnnnnn nnnnnnnnnn nnnnnnnnnn 29640
nnnnnnnnnn nnnnnnnnnn nnnnnnnnnn nnnnnnnnnn nnnnnnnnnn nnnnnnnnnn 29700
nnnnnnnnnn nnnnnnnnnn nnnnnnnnnn nnnnnnnnnn nnnnnnnnnn nnnnnnnnnn 29760
nnnnnnnnnn nnnnnnnnnn nnnnnnnnnn nnnnnnnnnn nnnnnnnnnn nnnnnnnnnn 29820
nnnnnnnnnn nnnnnnnnnn nnnnnnnnnn nnnnnnnnnn nnnnnnnnnn nnnnnnnnnn 29880
nnnnnnnnnn nnnnnnnnnn nnnnnnnnnn nnnnnnnnnn nnnnnnnnnn nnnnnnnnnn 29940
nnnnnnnnnn nnnnnnnnnn nnnnnnnnnn nnnnnnnnnn nnnnnnnnnn nnnnnnnnnn 30000
nnnnnnnnnn nnnnnnnnnn nnnnnnnnnn nnnnnnnnnn nnnnnnnnnn nnnnnnnnnn 30060
nnnnnnnnnn nnnnnnnnnn nnnnnnnnnn nnnnnnnnnn nnnnnnnnnn nnnnnnnnnn 30120
nnnnnnnnnn nnnnnnnnnn nnnnnnnnnn nnnnnnnnnn nnnnnnnnnn nnnnnnnnnn 30180
nnnnnnnnnn nnnnnnnnnn nnnnnnnnnn nnnnnnnnnn nnnnnnnnnn nnnnnnnnnn 30240
nnnnnnnnnn nnnnnnnnnn nnnnnnnnnn nnnnnnnnnn nnnnnnnnnn nnnnnnnnnn 30300
nnnnnnnnnn nnnnnnnnnn nnnnnnnnnn nnnnnnnnnn nnnnnnnnnn nnnnnnnnnn 30360
nnnnnnnnnn nnnnnnnnnn nnnnnnnnnn nnnnnnnnnn nnnnnnnnnn nnnnnnnnnn 30420
nnnnnnnnnn nnnnnnnnnn nnnnnnnnnn nnnnnnnnnn nnnnnnnnnn nnnnnnnnnn 30480
nnnnnnnnnn nnnnnnnnnn nnnnnnnnnn nnnnnnnnnn nnnnnnnnnn nnnnnnnnnn 30540
nnnnnnnnnn nnnnnnnnnn nnnnnnnnnn nnnnnnnnnn nnnnnnnnnn nnnnnnnnnn 30600
nnnnnnnnnn nnnnnnnnnn nnnnnnnnnn nnnnnnnnnn nnnnnnnnnn nnnnnnnnnn 30660
nnnnnnnnnn nnnnnnnnnn nnnnnnnnnn nnnnnnnnnn nnnnnnnnnn nnnnnnnnnn 30720
nnnnnnnnnn nnnnnnnnnn nnnnnnnnnn nnnnnnnnnn nnnnnnnnnn nnnnnnnnnn 30780
nnnnnnnnnn nnnnnnnnnn nnnnnnnnnn nnnnnnnnnn nnnnnnnnnn nnnnnnnnnn 30840
nnnnnnnnnn nnnnnnnnnn nnnnnnnnnn nnnnnnnnnn nnnnnnnnnn nnnnnnnnnn 30900
nnnnnnnnnn nnnnnnnnnn nnnnnnnnnn nnnnnnnnnn nnnnnnnnnn nnnnnnnnnn 30960
nnnnnnnnnn nnnnnnnnnn nnnnnnnnnn nnnnnnnnnn nnnnnnnnnn nnnnnnnnnn 31020
nnnnnnnnnn nnnnnnnnnn nnnnnnnnnn nnnnnnnnnn nnnnnnnnnn nnnnnnnnnn 31080
nnnnnnnnnn nnnnnnnnnn nnnnnnnnnn nnnnnnnnnn nnnnnnnnnn nnnnnnnnnn 31140
nnnnnnnnnn nnnnnnnnnn nnnnnnnnnn nnnnnnnnnn nnnnnnnnnn nnnnnnnnnn 31200
nnnnnnnnnn nnnnnnnnnn nnnnnnnnnn nnnnnnnnnn nnnnnnnnnn nnnnnnnnnn 31260
nnnnnnnnnn nnnnnnnnnn nnnnnnnnnn nnnnnnnnnn nnnnnnnnnn nnnnnnnnnn 31320
nnnnnnnnnn nnnnnnnnnn nnnnnnnnnn nnnnnnnnnn nnnnnnnnnn nnnnnnnnnn 31380
nnnnnnnnnn nnnnnnnnnn nnnnnnnnnn nnnnnnnnnn nnnnnnnnnn nnnnnnnnnn 31440
nnnnnnnnnn nnnnnnnnnn nnnnnnnnnn nnnnnnnnnn nnnnnnnnnn nnnnnnnnnn 31500

-continued

```
nnnnnnnnnn nnnnnnnnnn nnnnnnnnnn nnnnnnnnnn nnnnnnnnnn nnnnnnnnnn  31560
nnnnnnnnnn nnnnnnnnnn nnnnnnnnnn nnnnnnnnnn nnnnnnnnnn nnnnnnnnnn  31620
nnnnnnnnnn nnnnnnnnnn nnnnnnnnnn nnnnnnnnnn nnnnnnnnnn nnnnnnnnnn  31680
nnnnnnnnnn nnnnnnnnnn nnnnnnnnnn nnnnnnnnnn nnnnnnnnnn nnnnnnnnnn  31740
nnnnnnnnnn nnnnnnnnnn nnnnnnnnnn nnnnnnnnnn nnnnnnnnnn nnnnnnnnnn  31800
nnnnnnnnnn nnnnnnnnnn nnnnnnnnnn nnnnnnnnnn nnnnnnnnnn nnnnnnnnnn  31860
nnnnnnnnnn nnnnnnnnnn nnnnnnnnnn nnnnnnnnnn nnnnnnnnnn nnnnnnnnnn  31920
nnnnnnnnnn nnnnnnnnnn nnnnnnnnnn nnnnnnnnnn nnnnnnnnnn nnnnnnnnnn  31980
nnnnnnnnnn nnnnnnnnnn nnnnnnnnnn nnnnnnnnnn nnnnnnnnnn nnnnnnnnnn  32040
nnnnnnnnnn nnnnnnnnnn nnnnnnnnnn nnnnnnnnnn nnnnnnnnnn nnnnnnnnnn  32100
nnnnnnnnnn nnnnnnnnnn nnnnnnnnnn nnnnnnnnnn nnnnnnnnnn nnnnnnnnnn  32160
nnnnnnnnnn nnnnnnnnnn nnnnnnnnnn nnnnnnnnnn nnnnnnnnnn nnnnnnnnnn  32220
nnnnnnnnnn nnnnnnnnnn nnnnnnnnnn nnnnnnnnnn nnnnnnnnnn nnnnnnnnnn  32280
nnnnnnnnnn nnnnnnnnnn nnnnnnnnnn nnnnnnnnnn nnnnnnnnnn nnnnnnnnnn  32340
nnnnnnnnnn nnnnnnnnnn nnnnnnnnnn nnnnnnnnnn nnnnnnnnnn nnnnnnnnnn  32400
nnnnnnnnnn nnnnnnnnnn nnnnnnnnnn nnnnnnnnnn nnnnnnnnnn nnnnnnnnnn  32460
nnnnnnnnnn nnnnnnnnnn nnnnnnnnnn nnnnnnnnnn nnnnnnnnnn nnnnnnnnnn  32520
nnnnnnnnnn nnnnnnnnnn nnnnnnnnnn nnnnnnnnnn nnnnnnnnnn nnnnnnnnnn  32580
nnnnnnnnnn nnnnnnnnnn nnnnnnnnnn nnnnnnnnnn nnnnnnnnnn nnnnnnnnnn  32640
nnnnnnnnnn nnnnnnnnnn nnnnnnnnnn nnnnnnnnnn nnnnnnnnnn nnnnnnnnnn  32700
nnnnnnnnnn nnnnnnnnnn nnnnnnnnnn nnnnnnnnnn nnnnnnnnnn nnnnnnnnnn  32760
nnnnnnnnnn nnnnnnnnnn nnnnnnnnnn nnnnnnnnnn nnnnnnnnnn nnnnnnnnnn  32820
nnnnnnnnnn nnnnnnnnnn nnnnnnnnnn nnnnnnnnnn nnnnnnnnnn nnnnnnnnnn  32880
nnnnnnnnnn nnnnnnnnnn nnnnnnnnnn nnnnnnnnnn nnnnnnnnnn nnnnnnnnnn  32940
nnnnnnnnnn nnnnnnnnnn nnnnnnnnnn nnnnnnnnnn nnnnnnnnnn nnnnnnnnnn  33000
nnnnnnnnnn nnnnnnnnnn nnnnnnnnnn nnnnnnnnnn nnnnnnnnnn nnnnnnnnnn  33060
nnnnnnnnnn nnnnnnnnnn nnnnnnnnnn nnnnnnnnnn nnnnnnnnnn nnnnnnnnnn  33120
nnnnnnnnnn nnnnnnnnnn nnnnnnnnnn nnnnnnnnnn nnnnnnnnnn nnnnnnnnnn  33180
nnnnnnnnnn nnnnnnnnnn nnnnnnnnnn nnnnnnnnnn nnnnnnnnnn nnnnnnnnnn  33240
nnnnnnnnnn nnnnnnnnnn nnnnnnnnnn nnnnnnnnnn nnnnnnnnnn nnnnnnnnnn  33300
nnnnnnnnnn nnnnnnnnnn nnnnnnnnnn nnnnnnnnnn nnnnnnnnnn nnnnnnnnnn  33360
nnnnnnnnnn nnnnnnnnnn nnnnnnnnnn nnnnnnnnnn nnnnnnnnnn nnnnnnnnnn  33420
nnnnnnnnnn nnnnnnnnnn nnnnnnnnnn nnnnnnnnnn nnnnnnnnnn nnnnnnnnnn  33480
nnnnnnnnnn nnnnnnnnnn nnnnnnnnnn nnnnnnnnnn nnnnnnnnnn nnnnnnnnnn  33540
nnnnnnnnnn nnnnnnnnnn nnnnnnnnnn nnnnnnnnnn nnnnnnnnnn nnnnnnnnnn  33600
nnnnnnnnnn nnnnnnnnnn nnnnnnnnnn nnnnnnnnnn nnnnnnnnnn nnnnnnnnnn  33660
nnnnnnnnnn nnnnnnnnnn nnnnnnnnnn nnnnnnnnnn nnnnnnnnnn nnnnnnnnnn  33720
nnnnnnnnnn nnnnnnnnnn nnnnnnnnnn nnnnnnnnnn nnnnnnnnnn nnnnnnnnnn  33780
nnnnnnnnnn nnnnnnnnnn nnnnnnnnnn nnnnnnnnnn nnnnnnnnnn nnnnnnnnnn  33840
nnnnnnnnnn nnnnnnnnnn nnnnnnnnnn nnnnnnnnnn nnnnnnnnnn nnnnnnnnnn  33900
```

-continued

```
nnnnnnnnnn nnnnnnnnnn nnnnnnnnnn nnnnnnnnnn nnnnnnnnnn nnnnnnnnnn  33960
nnnnnnnnnn nnnnnnnnnn nnnnnnnnnn nnnnnnnnnn nnnnnnnnnn nnnnnnnnnn  34020
nnnnnnnnnn nnnnnnnnnn nnnnnnnnnn nnnnnnnnnn nnnnnnnnnn nnnnnnnnnn  34080
nnnnnnnnnn nnnnnnnnnn nnnnnnnnnn nnnnnnnnnn nnnnnnnnnn nnnnnnnnnn  34140
nnnnnnnnnn nnnnnnnnnn nnnnnnnnnn nnnnnnnnnn nnnnnnnnnn nnnnnnnnnn  34200
nnnnnnnnnn nnnnnnnnnn nnnnnnnnnn nnnnnnnnnn nnnnnnnnnn nnnnnnnnnn  34260
nnnnnnnnnn nnnnnnnnnn nnnnnnnnnn nnnnnnnnnn nnnnnnnnnn nnnnnnnnnn  34320
nnnnnnnnnn nnnnnnnnnn nnnnnnnnnn nnnnnnnnnn nnnnnnnnnn nnnnnnnnnn  34380
nnnnnnnnnn nnnnnnnnnn nnnnnnnnnn nnnnnnnnnn nnnnnnnnnn nnnnnnnnnn  34440
nnnnnnnnnn nnnnnnnnnn nnnnnnnnnn nnnnnnnnnn nnnnnnnnnn nnnnnnnnnn  34500
nnnnnnnnnn nnnnnnnnnn nnnnnnnnnn nnnnnnnnnn nnnnnnnnnn nnnnnnnnnn  34560
nnnnnnnnnn nnnnnnnnnn nnnnnnnnnn nnnnnnnnnn nnnnnnnnnn nnnnnnnnnn  34620
nnnnnnnnnn nnnnnnnnnn nnnnnnnnnn nnnnnnnnnn nnnnnnnnnn nnnnnnnnnn  34680
nnnnnnnnnn nnnnnnnnnn nnnnnnnnnn nnnnnnnnnn nnnnnnnnnn nnnnnnnnnn  34740
nnnnnnnnnn nnnnnnnnnn nnnnnnnnnn nnnnnnnnnn nnnnnnnnnn nnnnnnnnnn  34800
nnnnnnnnnn nnnnnnnnnn nnnnnnnnnn nnnnnnnnnn nnnnnnnnnn nnnnnnnnnn  34860
nnnnnnnnnn nnnnnnnnnn nnnnnnnnnn nnnnnnnnnn nnnnnnnnnn nnnnnnnnnn  34920
nnnnnnnnnn nnnnnnnnnn nnnnnnnnnn nnnnnnnnnn nnnnnnnnnn nnnnnnnnnn  34980
nnnnnnnnnn nnnnnnnnnn nnnnnnnnnn nnnnnnnnnn nnnnnnnnnn nnnnnnnnnn  35040
nnnnnnnnnn nnnnnnnnnn nnnnnnnnnn nnnnnnnnnn nnnnnnnnnn nnnnnnnnnn  35100
nnnnnnnnnn nnnnnnnnnn nnnnnnnnnn nnnnnnnnnn nnnnnnnnnn nnnnnnnnnn  35160
nnnnnnnnnn nnnnnnnnnn nnnnnnnnnn nnnnnnnnnn nnnnnnnnnn nnnnnnnnnn  35220
nnnnnnnnnn nnnnnnnnnn nnnnnnnnnn nnnnnnnnnn nnnnnnnnnn nnnnnnnnnn  35280
nnnnnnnnnn nnnnnnnnnn nnnnnnnnnn nnnnnnnnnn nnnnnnnnnn nnnnnnnnnn  35340
nnnnnnnnnn nnnnnnnnnn nnnnnnnnnn nnnnnnnnnn nnnnnnnnnn nnnnnnnnnn  35400
nnnnnnnnnn nnnnnnnnnn nnnnnnnnnn nnnnnnnnnn nnnnnnnnnn nnnnnnnnnn  35460
nnnnnnnnnn nnnnnnnnnn nnnnnnnnnn nnnnnnnnnn nnnnnnnnnn nnnnnnnnnn  35520
nnnnnnnnnn nnnnnnnnnn nnnnnnnnnn nnnnnnnnnn nnnnnnnnnn nnnnnnnnnn  35580
nnnnnnnnnn nnnnnnnnnn nnnnnnnnnn nnnnnnnnnn nnnnnnnnnn nnnnnnnnnn  35640
nnnnnnnnnn nnnnnnnnnn nnnnnnnnnn nnnnnnnnnn nnnnnnnnnn nnnnnnnnnn  35700
nnnnnnnnnn nnnnnnnnnn nnnnnnnnnn nnnnnnnnnn nnnnnnnnnn nnnnnnnnnn  35760
nnnnnnnnnn nnnnnnnnnn nnnnnnnnnn nnnnnnnnnn nnnnnnnnnn nnnnnnnnnn  35820
nnnnnnnnnn nnnnnnnnnn nnnnnnnnnn nnnnnnnnnn nnnnnnnnnn nnnnnnnnnn  35880
nnnnnnnnnn nnnnnnnnnn nnnnnnnnnn nnnnnnnnnn nnnnnnnnnn nnnnnnnnnn  35940
nnnnnnnnnn nnnnnnnnnn nnnnnnnnnn nnnnnnnnnn nnnnnnnnnn nnnnnnnnnn  36000
nnnnnnnnnn nnnnnnnnnn nnnnnnnnnn nnnnnnnnnn nnnnnnnnnn nnnnnnnnnn  36060
nnnnnnnnnn nnnnnnnnnn nnnnnnnnnn nnnnnnnnnn nnnnnnnnnn nnnnnnnnnn  36120
nnnnnnnnnn nnnnnnnnnn nnnnnnnnnn nnnnnnnnnn nnnnnnnnnn nnnnnnnnnn  36180
nnnnnnnnnn nnnnnnnnnn nnnnnnnnnn nnnnnnnnnn nnnnnnnnnn nnnnnnnnnn  36240
```

-continued

```
nnnnnnnnnn nnnnnnnnnn nnnnnnnnnn nnnnnnnnnn nnnnnnnnnn nnnnnnnnnn  36300
nnnnnnnnnn nnnnnnnnnn nnnnnnnnnn nnnnnnnnnn nnnnnnnnnn nnnnnnnnnn  36360
nnnnnnnnnn nnnnnnnnnn nnnnnnnnnn nnnnnnnnnn nnnnnnnnnn nnnnnnnnnn  36420
nnnnnnnnnn nnnnnnnnnn nnnnnnnnnn nnnnnnnnnn nnnnnnnnnn nnnnnnnnnn  36480
nnnnnnnnnn nnnnnnnnnn nnnnnnnnnn nnnnnnnnnn nnnnnnnnnn nnnnnnnnnn  36540
nnnnnnnnnn nnnnnnnnnn nnnnnnnnnn nnnnnnnnnn nnnnnnnnnn nnnnnnnnnn  36600
nnnnnnnnnn nnnnnnnnnn nnnnnnnnnn nnnnnnnnnn nnnnnnnnnn nnnnnnnnnn  36660
nnnnnnnnnn nnnnnnnnnn nnnnnnnnnn nnnnnnnnnn nnnnnnnnnn nnnnnnnnnn  36720
nnnnnnnnnn nnnnnnnnnn nnnnnnnnnn nnnnnnnnnn nnnnnnnnnn nnnnnnnnnn  36780
nnnnnnnnnn nnnnnnnnnn nnnnnnnnnn nnnnnnnnnn nnnnnnnnnn nnnnnnnnnn  36840
nnnnnnnnnn nnnnnnnnnn nnnnnnnnnn nnnnnnnnnn nnnnnnnnnn nnnnnnnnnn  36900
nnnnnnnnnn nnnnnnnnnn nnnnnnnnnn nnnnnnnnnn nnnnnnnnnn nnnnnnnnnn  36960
nnnnnnnnnn nnnnnnnnnn nnnnnnnnnn nnnnnnnnnn nnnnnnnnnn nnnnnnnnnn  37020
nnnnnnnnnn nnnnnnnnnn nnnnnnnnnn nnnnnnnnnn nnnnnnnnnn nnnnnnnnnn  37080
nnnnnnnnnn nnnnnnnnnn nnnnnnnnnn nnnnnnnnnn nnnnnnnnnn nnnnnnnnnn  37140
nnnnnnnnnn nnnnnnnnnn nnnnnnnnnn nnnnnnnnnn nnnnnnnnnn nnnnnnnnnn  37200
nnnnnnnnnn nnnnnnnnnn nnnnnnnnnn nnnnnnnnnn nnnnnnnnnn nnnnnnnnnn  37260
nnnnnnnnnn nnnnnnnnnn nnnnnnnnnn nnnnnnnnnn nnnnnnnnnn nnnnnnnnnn  37320
nnnnnnnnnn nnnnnnnnnn nnnnnnnnnn nnnnnnnnnn nnnnnnnnnn nnnnnnnnnn  37380
nnnnnnnnnn nnnnnnnnnn nnnnnnnnnn nnnnnnnnnn nnnnnnnnnn nnnnnnnnnn  37440
nnnnnnnnnn nnnnnnnnnn nnnnnnnnnn nnnnnnnnnn nnnnnnnnnn nnnnnnnnnn  37500
nnnnnnnnnn nnnnnnnnnn nnnnnnnnnn nnnnnnnnnn nnnnnnnnnn nnnnnnnnnn  37560
nnnnnnnnnn nnnnnnnnnn nnnnnnnnnn nnnnnnnnnn nnnnnnnnnn nnnnnnnnnn  37620
nnnnnnnnnn nnnnnnnnnn nnnnnnnnnn nnnnnnnnnn nnnnnnnnnn nnnnnnnnnn  37680
nnnnnnnnnn nnnnnnnnnn nnnnnnnnnn nnnnnnnnnn nnnnnnnnnn nnnnnnnnnn  37740
nnnnnnnnnn nnnnnnnnnn nnnnnnnnnn nnnnnnnnnn nnnnnnnnnn nnnnnnnnnn  37800
nnnnnnnnnn nnnnnnnnnn nnnnnnnnnn nnnnnnnnnn nnnnnnnnnn nnnnnnnnnn  37860
nnnnnnnnnn nnnnnnnnnn nnnnnnnnnn nnnnnnnnnn nnnnnnnnnn nnnnnnnnnn  37920
nnnnnnnnnn nnnnnnnnnn nnnnnnnnnn nnnnnnnnnn nnnnnnnnnn nnnnnnnnnn  37980
nnnnnnnnnn nnnnnnnnnn nnnnnnnnnn nnnnnnnnnn nnnnnnnnnn nnnnnnnnnn  38040
nnnnnnnnnn nnnnnnnnnn nnnnnnnnnn nnnnnnnnnn nnnnnnnnnn nnnnnnnnnn  38100
nnnnnnnnnn nnnnnnnnnn nnnnnnnnnn nnnnnnnnnn nnnnnnnnnn nnnnnnnnnn  38160
nnnnnnnnnn nnnnnnnnnn nnnnnnnnnn nnnnnnnnnn nnnnnnnnnn nnnnnnnnnn  38220
nnnnnnnnnn nnnnnnnnnn nnnnnnnnnn nnnnnnnnnn nnnnnnnnnn nnnnnnnnnn  38280
nnnnnnnnnn nnnnnnnnnn nnnnnnnnnn nnnnnnnnnn nnnnnnnnnn nnnnnnnnnn  38340
nnnnnnnnnn nnnnnnnnnn nnnnnnnnnn nnnnnnnnnn nnnnnnnnnn nnnnnnnnnn  38400
nnnnnnnnnn nnnnnnnnnn nnnnnnnnnn nnnnnnnnnn nnnnnnnnnn nnnnnnnnnn  38460
nnnnnnnnnn nnnnnnnnnn nnnnnnnnnn nnnnnnnnnn nnnnnnnnnn nnnnnnnnnn  38520
nnnnnnnnnn nnnnnnnnnn nnnnnnnnnn nnnnnnnnnn nnnnnnnnnn nnnnnnnnnn  38580
nnnnnnnnnn nnnnnnnnnn nnnnnnnnnn nnnnnnnnnn nnnnnnnnnn nnnnnnnnnn  38640
```

-continued

```
nnnnnnnnnn nnnnnnnnnn nnnnnnnnnn nnnnnnnnnn nnnnnnnnnn nnnnnnnnnn  38700
nnnnnnnnnn nnnnnnnnnn nnnnnnnnnn nnnnnnnnnn nnnnnnnnnn nnnnnnnnnn  38760
nnnnnnnnnn nnnnnnnnnn nnnnnnnnnn nnnnnnnnnn nnnnnnnnnn nnnnnnnnnn  38820
nnnnnnnnnn nnnnnnnnnn nnnnnnnnnn nnnnnnnnnn nnnnnnnnnn nnnnnnnnnn  38880
nnnnnnnnnn nnnnnnnnnn nnnnnnnnnn nnnnnnnnnn nnnnnnnnnn nnnnnnnnnn  38940
nnnnnnnnnn nnnnnnnnnn nnnnnnnnnn nnnnnnnnnn nnnnnnnnnn nnnnnnnnnn  39000
nnnnnnnnnn nnnnnnnnnn nnnnnnnnnn nnnnnnnnnn nnnnnnnnnn nnnnnnnnnn  39060
nnnnnnnnnn nnnnnnnnnn nnnnnnnnnn nnnnnnnnnn nnnnnnnnnn nnnnnnnnnn  39120
nnnnnnnnnn nnnnnnnnnn nnnnnnnnnn nnnnnnnnnn nnnnnnnnnn nnnnnnnnnn  39180
nnnnnnnnnn nnnnnnnnnn nnnnnnnnnn nnnnnnnnnn nnnnnnnnnn nnnnnnnnnn  39240
nnnnnnnnnn nnnnnnnnnn nnnnnnnnnn nnnnnnnnnn nnnnnnnnnn nnnnnnnnnn  39300
nnnnnnnnnn nnnnnnnnnn nnnnnnnnnn nnnnnnnnnn nnnnnnnnnn nnnnnnnnnn  39360
nnnnnnnnnn nnnnnnnnnn nnnnnnnnnn nnnnnnnnnn nnnnnnnnnn nnnnnnnnnn  39420
nnnnnnnnnn nnnnnnnnnn nnnnnnnnnn nnnnnnnnnn nnnnnnnnnn nnnnnnnnnn  39480
nnnnnnnnnn nnnnnnnnnn nnnnnnnnnn nnnnnnnnnn nnnnnnnnnn nnnnnnnnnn  39540
nnnnnnnnnn nnnnnnnnnn nnnnnnnnnn nnnnnnnnnn nnnnnnnnnn nnnnnnnnnn  39600
nnnnnnnnnn nnnnnnnnnn nnnnnnnnnn nnnnnnnnnn nnnnnnnnnn nnnnnnnnnn  39660
nnnnnnnnnn nnnnnnnnnn nnnnnnnnnn nnnnnnnnnn nnnnnnnnnn nnnnnnnnnn  39720
nnnnnnnnnn nnnnnnnnnn nnnnnnnnnn nnnnnnnnnn nnnnnnnnnn nnnnnnnnnn  39780
nnnnnnnnnn nnnnnnnnnn nnnnnnnnnn nnnnnnnnnn nnnnnnnnnn nnnnnnnnnn  39840
nnnnnnnnnn nnnnnnnnnn nnnnnnnnnn nnnnnnnnnn nnnnnnnnnn nnnnnnnnnn  39900
nnnnnnnnnn nnnnnnnnnn nnnnnnnnnn nnnnnnnnnn nnnnnnnnnn nnnnnnnnnn  39960
nnnnnnnnnn nnnnnnnnnn nnnnnnnnnn nnnnnnnnnn                        40000
```

METHOD OF REDUCING ANTIGENIC DRIFT OR REASSORTMENT OF VIRUSES IN A HOST ANIMAL USING α INTERFERON

CROSS REFERENCE TO RELATED APPLICATIONS

This application is the U.S. national phase of International Application No. PCT/US2014/052079, Filed Aug. 21, 2014, which designated the U.S. and claims the benefit of priority from U.S. provisional patent application No. 61/868,292 filed Aug. 21, 2013, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Dec. 8, 2017, is named 51-735 SL.txt and is 53,623 bytes in size.

FIELD OF THE INVENTION

The inventions relate to a novel method of reducing antigenic drift or reassortment of viruses in a host animal comprising administering to the host animal α-interferon. More specifically, it involves the use of natural human interferon (α-n3) against viruses that include both wild-type and oseltamivir-resistant, avian-origin influenza A (H7N9). The invention further relates to a novel method for preventing, treating or reducing the symptoms of an NA-292R H7N9 influenza infection, NA-292K H7N9 influenza infection or a viral combination thereof.

BACKGROUND OF THE INVENTION

Influenza A(H7N9) is an emerging avian influenza strain highly pathogenic in humans. Patients have exhibited symptoms including viral pneumonia, acute kidney failure, acute respiratory distress syndrome, diffuse intravascular coagulation and septic shock.

Although A(H7N9) can be highly virulent in humans, in poultry A(H7N9) produces very few, if any, symptoms. This unusual property makes this outbreak harder to detect and monitor, which leads experts to remain fearful of the possibility of the virus mutating into a form easily transmissible between humans. To date there has been no confirmation of human-to-human transmission, but the need for proactive measures continues to persist. A recent study has shown that A(H7N9) strains with a dominant K292 (i.e. 292K or 292-K H7N9) were resistant to zanamivir, peramivir, and oseltamivir, although resistance can be masked by a mixed R/K viral population (Yen et al., mBio 4: e00396-13, 2013). The present research and invention provides a novel method of addressing at least the need arising from this emergent threat in the field of the invention.

As known, influenza virus, including its many strain and subtypes, may cause disease in the upper and lower respiratory tracts. Influenza viruses are dynamic and are continuously evolving. Influenza viruses can change in two different ways: antigenic drift and antigenic shift. Influenza viruses are changing by antigenic drift all the time, but antigenic shift happens only occasionally. Influenza type A viruses undergo both kinds of changes; influenza type B viruses change only by the more gradual process of antigenic drift.

The constant threat of mutation makes the emergence of an influenza pandemic unpredictable and no universal influenza vaccine is available so far. The licensed anti-influenza drugs (M2-ion channel blockers and neuraminidase inhibitors) are limited in clinical treatment of infected patients because of rapid emergence of drug-resistant mutations in the targeted genes. One of the concerns of a potential influenza pandemic is high mortality (e.g., H5N1, H7N9). The rapid disease progression characteristic of pandemic influenza viruses and the emergence of resistance to inhibitors of viral function will require other approaches to limit or terminate disease and spread the virus.

Additionally, the lengthy development time and limited production capability of conventional inactivated influenza vaccines could severely hinder the ability to control the pandemic spread of avian influenza through vaccination. Thus, there is a need in the art for a method of suppressing antigenic mutation (antigenic drift) and antigenic reassortment of viruses in a host—such as an animal or human host. At the same time, there is also a need to evolve novel methods including synergistic approaches to combat these newly uncovered genetically re-assorted viruses, which in some cases, may have become resistant to known vaccines and treatments.

BRIEF SUMMARY OF THE INVENTION

The present invention relates to a method for preventing or reducing antigenic drift or viral reassortment in a host animal comprising determining if a host animal has been exposed to or infected by an avian influenza virus, administering to the exposed host animal α-interferon.

Specifically, the avian influenza virus may be influenza A (H7N9), which is commonly found in poultry and is an emerging influenza strain that is highly pathogenic in humans and can result in viral pneumonia, acute kidney failure, acute respiratory distress syndrome, diffuse intravascular coagulation and septic shock.

The goal of a number of the experiments and examples contained herein is to determine the mechanism of virulence of viruses in veterinary or other host populations, the modes to transmission to man, and to modify the processes through biological interventions/therapy. To accomplish the goals, three parameters considered are the suitable biological models to test the hypotheses of virulence and transmission to man, the range of analytical techniques to study the phenomenon such as reassortment and mutation which occur in influenza strains or more specifically the influenza subtype and a scientific assessment of the potential of therapies to prevent or slow reassortment and transmission first in in-vitro studies and then in in-vivo experiments. The invention therefore relates at least to applying these three parameters to both wild-type and mutant H7N9 influenza.

One preferred embodiment of the method comprises the steps of identifying a patient infected with NA-292R H7N9 influenza, NA-292K H7N9 influenza or a combination thereof; detecting in said NA-292R H7N9 influenza, NA-292K H7N9 influenza or said combination thereof neuraminidase-inhibitor resistance; and administering to said patient α-interferon.

DETAILED DESCRIPTION OF THE INVENTION

Figure 1:
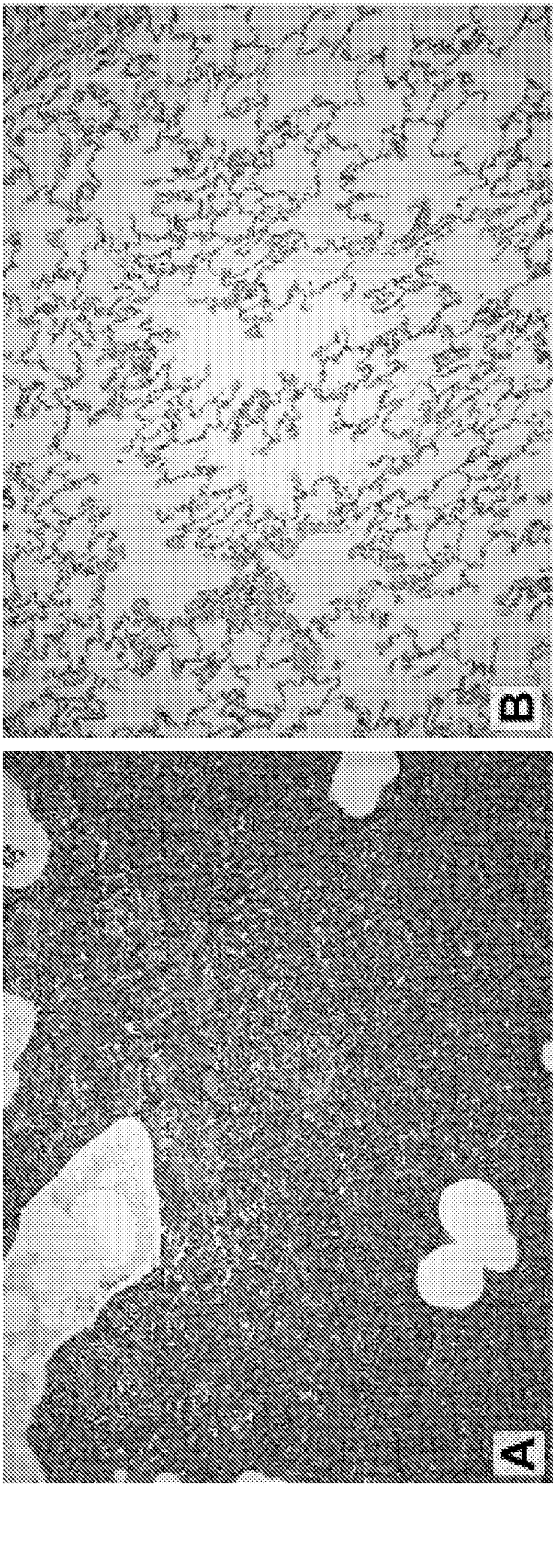
FIG. 1 shows two side-by-side pulmonary photomicrographs comparing tissue damage resulting from atypical pneumonia in ALFERON LDO (B) vs. placebo treatment (A).

Having generally described influenza A(H7N9) including NA-292K H7N9 and NA-292K H7N9 influenza in the Background section, the present inventors determined to find a method for addressing antigenic drift, viral reassortment and prevention or treatment of symptoms in a host animal.

Antigenic drift refers to small, gradual changes that occur through point mutations in the two genes that contain the genetic material to produce the main surface proteins, hemagglutinin, and neuraminidase. These point mutations occur unpredictably and result in minor changes to these surface proteins. Antigenic drift produces new virus strains that may not be recognized by antibodies to earlier influenza strains. This process works as follows: a person (or a non human host animal) infected with a particular influenza virus strain develops antibody against that strain. As newer virus strains appear, the antibodies against the older strains might not recognize the “newer” virus, and infection with a new strain can occur. This is one of the main reasons why people can become infected with influenza viruses more than one time and why global surveillance is critical in order to monitor the evolution of human influenza virus stains for selection of which strains should be included in the annual production of influenza vaccine.

Antigenic shift refers to an abrupt, major change to produce a novel influenza A virus subtype in humans that was not currently circulating among people. Antigenic shift can occur either through direct animal-to-human (such as poultry, swine or other animal) transmission or through mixing of human influenza A and animal influenza A virus genes to create a new human influenza A subtype virus through a process called genetic reassortment. For example, because naturally occurring reassortant viruses derived from different host species have been recovered from pigs they have been considered to be a mixing vessel supporting potential influenza virus reassortment (Scholtissek/1994). Antigenic shift results in a new human influenza A subtype, which, under the right conditions could cause global influenza pandemic resulting from worldwide spread.

Vaccination is a very efficient way to prevent influenza infection; however, no commercial vaccine specific for H7N9 is currently available. Moreover, humans lack any immunological memory against H7N9, which is another concern of its potential to result in a pandemic if easy human-to-human transmission becomes a trait of the virus. Antiviral treatment is an important strategy in helping to control and prevent influenza infections. As recommended by the CDC in Atlanta, USA, antiviral treatment against influenza infections should be applied as early as possible, ideally within 48 hour after onset of illness. Some antiviral drugs, used in the treatment of other viruses are available to treat influenza infections and some have suggested their application to this novel H7N9 virus. For influenza infections, M2-ion channel blockers (e.g., amantadine and rimantadine) and neuraminidase inhibitors (e.g., oseltamivir, zanamivir and peramivir) are some of the used antiviral drugs, and these compounds are approved by the United Stated Food and Drug Administration. However, the H7N9 is resistant to both amantadine and rimantadine because an S31N mutation exists in the M2 protein, which confers M2-ion channel blocker resistance. As a result, neuraminidase inhibitors are the only FDA-approved compounds that can be used for the treatment of the novel H7N9 infection and other M2-ion channel blocker-resistant influenza viruses.

For general analysis, nasal swab samples were amplified directly and RNA was extracted from the amplified samples and BALF (bronchoalveolar lavage fluid). A reverse transcription-polymerase chain reaction was conducted to amplify each segment and polymerase chain reaction (PCR) products were characterized by restriction enzyme digestion and sequencing. For individual analysis, a single virion was plaque purified three times from the amplified nasal swabs (approx. ten plaques per nasal swab) and BALFs (approx. ten plaques per BALF sample), and then each segment of the viral genome was amplified and characterized by restriction enzyme digestion and sequencing as the general analysis. All gene segments of transmissible viruses were compared with those of the parental viruses and the viruses isolated from co-infected hosts. This allowed a determination of the genetic components of successfully transmissible viruses.

Genetically, analysis shows that the novel H7N9 virus is a triple reassortant virus carrying genes from H7N3, H9N2 and H11N9 or H2N9 avian influenza A viruses. It is assumed that the novel H7N9 subtype virus was generated by a single or double independent genetic reassortment event in ducks or chickens in China (Lam T T, Wang J, Shen Y, et al.). The genesis and source of the H7N9 influenza viruses causing human infections in China (Nature 2013; 502(7470):241-4). Notably, the novel H7N9 virus replicated efficiently in both upper and lower respiratory tracts of infected nonhuman primates (Cynomolgus macaques). This is troubling as tissue damage, including damage to the lungs resulting from pneumonia, is the principal factor in the lethality of pandemic flu. This knowledge only furthers the desire for novel treatments or new synergistic treatments to combat newly uncovered genetically re-assorted and drug resistant viruses. Examination of lung pathology in avian influenza is summarized in U.S. Pat. No. 8,075,877, which is hereby incorporated by reference in its entirety.

Natural influenza infection by this virus is usually initiated by relatively low levels of the virus in the respiratory tract via the oral cavity or the nasal passage. Virions of influenza virus will randomly disperse among susceptible epithelial cells and dendritic cells and a series of stochastic events result in the initial successful infection of relatively few cells. It is important to note, that it is at this time, the administration of compositions of the disclosure including α-interferon during this very early phase of viral pathogenesis would significantly influence the outcome of infection by direct or indirect inhibition of viral multiplication in infected cells and to recognize that this strategy is may reduces the number of susceptible cells that will be infected in later rounds of infection.

In a study conducted to determine the efficacy of a specific α-interferon against avian infection in non-human primates, cynomolgus macaques (*Macaca fascicularis*) infected with influenza virus, demonstrated that the clinical signs in the macaques resemble those found in humans infected with the same virus, thus allowing the infection of cynomolgus macaques to serve as a model for these infections in humans (Rimmelzwaan et al. Avian Dis. 2003; 47(3 Suppl):931-3, Kuiken et al. Vet Pathol. 2003 May; 40(3):304-10, Rimmelzwaan et al. J. Virol. 2001 July; 75(14):6687-91).

Briefly, in the macaque infection model described above, upon euthanasia at day 5, infection macroscopic lung lesions indicated that animals treated with a specific α-interferon showed no separated dark red area(s) or diffuse dark areas on the lungs in contrast to animals of the other groups. This is consistent with the microscopic findings which indicate also a lower grade of primary atypical pneumonia in both left cranial- and caudal lung lobes in animals of this group.

Prophylactic treatment of macaques with oro-mucosal delivery of this α-interferon appears to have a beneficial dose dependent effect with reduced gross- and histo pathology in treated animals.

Exposure of the oromucosa of a patient (also a subject or host) to α-interferon including low dose oral α-interferon such as ALFERON LDO, therefore, may to lead to biological effects in humans and animals including a systemic antiviral effect. A naturally derived α-interferon, ALFERON N Injection, has been approved for treatment of Condylomata acuminata. It is active at doses significantly lower than those used for recombinant α-interferon.

ALFERON, a natural α-n3 human leukocyte interferon, commercially available as, for example, as ALFERON N Injection and as an experimental drug, ALFERON LDO, from HEMISPHERX BIOPHARMA, Inc. of PA, USA (referred to herein as ALFERON) is a specific α-interferon component and is the only FDA approved multi-species, natural α-interferon available in the United States. It is the first natural source, multi-species interferon and is a consistent mixture of at least seven species of α-interferon. The α-interferon is specific preferably natural α-n3 human leukocyte interferon, a natural cocktail of at least seven species of human α-interferon. In contrast, the other available α-interferons are single molecular species of α-interferon made in bacteria using DNA recombinant technology. These single molecular species of α-interferon also lack an important structural carbohydrate component because this glycosylation step is not performed during the bacterial process. Reverse phase HPLC studies show that ALFERON N Injection is a consistent mixture of at least seven species of α-interferon (α2, α4, α7, α8, α10, α16 and α17). This natural-source interferon has unique anti-viral properties distinguishing it from genetically engineered interferons. Multiple clinical studies and drug trials also suggests that ALFERON has broad antiviral activity as summarized in the table below.

TABLE A

| Disease | Source |
|---|---|
| Condylomata acuminata (HPV-Genital Lesion) | Approved Indication, Klutke J J (1995) |
| HPV-Anal Lesion | Fleshner, P R (1994) |
| HIV | Phase 3, BB-IND 5734 |
| Chronic Hepatitis C | Phase 3, BB-IND 4746 |
| HIV & HCV Co-infection | Phase 2, BB-IND 4746 |
| Multiple Sclerosis | Onufer J A (2001) |
| Vulvar Vestibulitis | Hoffman R G (2003) |
| Subacute Panencephalitis (SSPE), Measles | Phase 1/2 BB-IND 2473 |

ALFERON Low Dose Oral (LDO) formulation for mucosal administration has been tested in Phase I and has an FDA approved 200+patient Phase II clinical study protocol for the prophylaxis and treatment of seasonal and pandemic influenza. It is also important to note that ALFERON LDO is biologically active in multiple animal species including in pigs, chicken (poultry) and bovine against coronavirus, heat challenge, and bovine respiratory disease complex, respectively. Briefly, the minute doses bind to mucosal interferon receptors triggering broad immune response and the presumed mechanism of action is to bind to interferon receptors on the oral mucosal membrane leading to inhibition of viral RNA transcription, inhibition of viral protein synthesis, blockage of viral replication, promotion of apoptosis in virus-infected cells and enhancement of immune responses. Other available interferon is contraindicated for use by oral mucosal delivery routes because of the danger of neutralizing antibody formation. These neutralizing antibodies may create life-threatening situations since interferon is the body's first line of defense against airborne viruses.

In studies in SARS, as a case-study for the relative potency of the purified interferon was tested against other interferons and was concluded to be the most active interferon at clinically achievable serum levels that does not induce neutralizing antibodies (Tan et al., Emerg. Infect. Dis. 10:581-586, 2004).

The high purity of ALFERON N Injection and its advantage as a natural mixture of seven interferon species, some of which, like species 8b, have greater antiviral activities than other species, for example, species 2b, which is the only component of INTRON A®. The superior antiviral activities, for example in the treatment of chronic hepatitis C virus (HCV) and HIV infection, and tolerability of ALFERON N Injection compared to other available recombinant interferons, such as INTRON A® and ROFERON A®, have been reported.

The compositions of the disclosure, including mixtures thereof, (including interferon or α-interferon) may be administered in any of the methods of the disclosure by any suitable route, such as, for example, oral, topical (including trans-dermal, buccal and sublingual), parenteral, vaginal, rectal, and nasal. For internal administration the α-interferon may, for example, be formulated in conventional manner for oral, nasal or buccal administration.

Formulations for internal administration include aqueous solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents.

Parenteral administration may include subcutaneous, intramuscular, intravenous, intradermal, intrathecal epidural, and intraperitoneal administrations. It will be appreciated that the preferred route will vary with the condition and age of the recipient, the nature of the infection and the chosen active ingredient.

The recommended dosage of the components will depend on the clinical status of the patient and the experience of the clinician in treating similar infection. As a general guideline, dosage of α-interferon (e.g., ALFERON N INJECTION or ALFERON LDO) utilized in any method of the disclosure may be from 1000 units to 10,000,000 units per day. Orally and intranasally, the administration can be within a concentration of 1,000 IU/ml to 10,000 IU/ml. ALFERON may be administered once, twice or three times weekly or every other day so that the average daily dose is within the above limits. For some embodiments of systemic infections, 5 to 10 million units (sq) thrice weekly may be used.

For ALFERON N Injection, experience to date is with dosages above 3 IU/lb of patient body weight, but more specifically dosages of 1,000 IU to 10,000,000 IU per dose are envisioned. ALFERON N Injection is available as an injectable solution containing 5,000,000 international units (IU) per ml. Oral α-interferon (ALFERON LDO) has been administered as a liquid solution in the range of 500-10,000 IU/day and calculated on the basis of a 150 pound human this is from 3.3 to 66.0 IU/lb per day and experience to date indicates beneficial results can be obtained at dosage levels of α-interferon in excess of 450 IU, that is greater than 3 IU/pound body weight. Concentrations of 1,000 IU/ml to 10,000 IU/ml are specifically envisioned in one preferred embodiment of the invention and represent the minimum range envisioned in synergistic applications. Under specific conditions, a healthcare provider would be able to determine the optimal dose and schedule.

Natural infection by this virus is usually initiated with relatively small inoculums of virion (e.g., $10^2$-$10^5$ PFU). Upon entry into the respiratory tract via the oral cavity or the nasal passage, virions of influenza virus will be dispersed among susceptible epithelial cells and dendritic cells. This is a series of stochastic events that result in the initial successful infection of relatively few cells. Administration of compositions of the disclosure including α-interferon during this very early phase of viral pathogenesis would significantly influence the outcome of infection by direct or indirect inhibition of viral multiplication in infected cells. Non-infected epithelial and dendritic cells can be induced to produce α/β-IFNs through the action of α-interferon.

The key point in this strategy is that the development of clinical disease as an outcome of naturally occurring infection requires amplification of the initial viral inoculum within the host. Early administration of α-interferon effectively reduces the number of susceptible cells that will be infected in later rounds of infection. Experiments on pandemic flu conducted at Viroclinics Biosciences in the Netherlands has shown tissue damage is the principal factor in the lethality of pandemic flu (See FIG. 1). FIG. 1 shows a pulmonary photomicrographs comparing tissue damage resulting from atypical pneumonia in ALFERON LDO vs. placebo treatment. The images are taken from hosts infected with highly pathogenic influenza at 5-days post infection. The placebo treatment (frame A) is shown on the left and resulted in severe atypical pneumonia, but with treatment (frame B) with ALFERON LDO resulted in marginal atypical pneumonia. This shows that the treatment can cause dramatic sparing of tissue damage, resulting in reduced lethality. Also, since avian influenza virus is known to infect cells in the gastric mucosa, it is very important to intervene with effective drugs that can act locally in the respiratory tract and systemically. Amplification of virus can occur in a number of organs and tissues. Usually primary or secondary viremias occur between rounds of viral multiplication. Early, effective and sustained therapeutic intervention is expected to reduce the severity and duration of disease.

Figure 2:
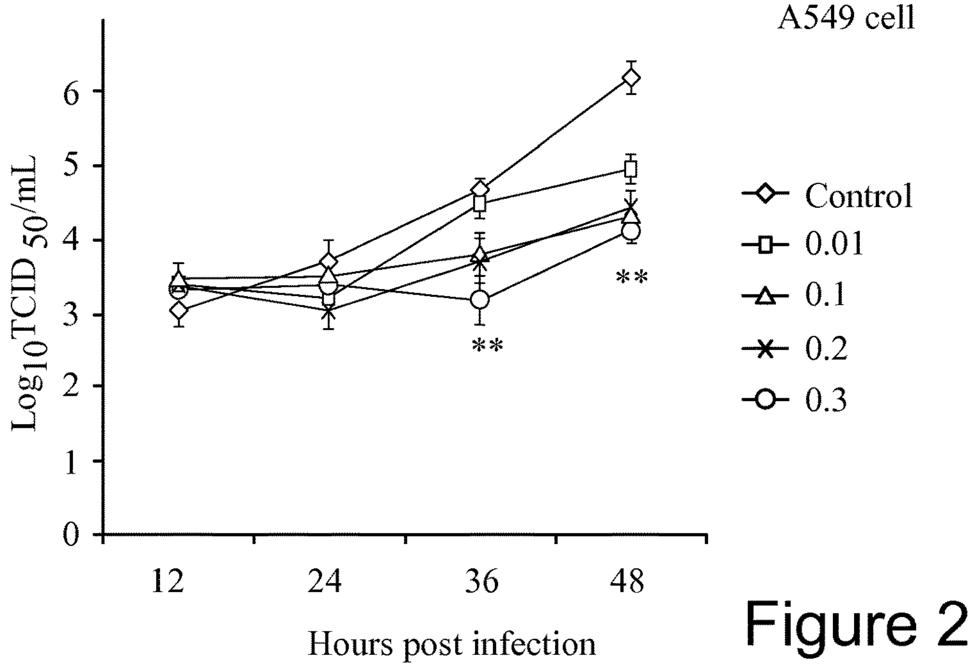
FIG. 2 is a graphical representation showing that oseltamivir (Tamiflu) is effective against wild-type Anhui-1 (A/Anhui/1/2013).
Figure 3:
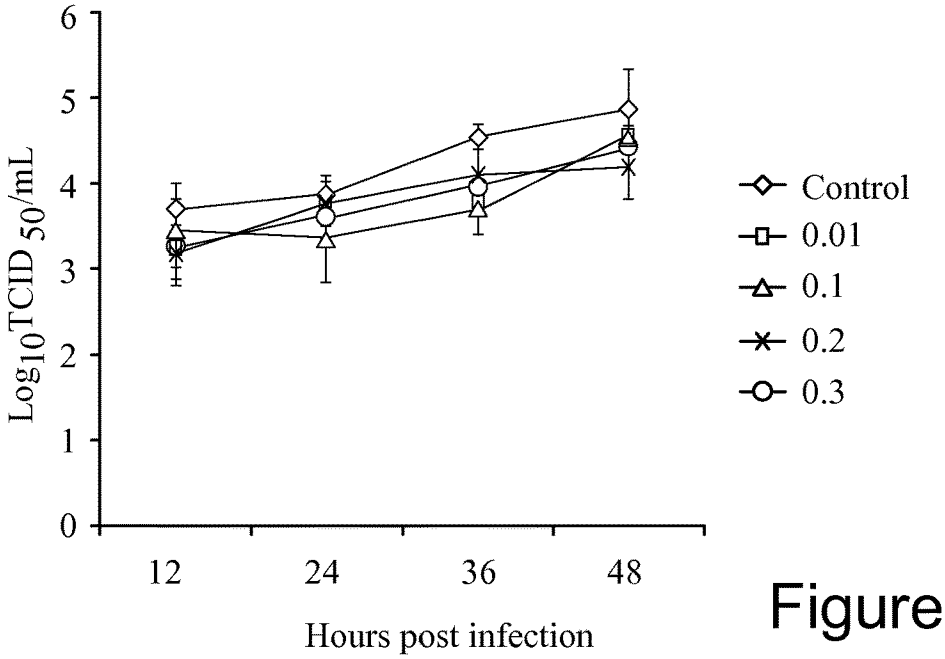
FIG. 3 is a graphical representation showing that mutant (A/Shanghai/1/2013 with NA-292K; Shanghai 1-NA292K) shows resistance to oseltamivir (Tamiflu).

The efficacy of some treatments can be adversely affected by the mechanisms of antigenic drift or viral reassortment, as described above. For example, the antiviral oseltamivir, the first orally active neuraminidase inhibitor commercially developed, is ineffective against mutant A/Shanghai/1/2013 with NA-292K (See FIG. 2). FIG. 2 is a graphical representation showing that oseltamivir (Tamiflu) is effective against wildtype Anhui-1 (A/Anhui/1/2013), but that mutant (A/Shanghai/1/2013 with NA-292K; Shanghai 1-NA292K) shows resistance. Clinical studies had shown that oseltamivir treatment could reduce the viral load in the respiratory tract of patients with H7N9 infection (Hu Y, Lu S, Song Z, et al., Association between adverse clinical outcome in human disease caused by novel influenza A H7N9 virus and sustained viral shedding and emergence of antiviral resistance (Lancet 2013; 381(9885):2273-9). However, some patients with oseltamivir treatment failure had a poor clinical outcome. Further studies confirmed that H7N9 isolates with a dominant 292K genotype are resistant to zanamivir, peramivir and oseltamivir although this resistance can be masked by a mixed R/K genotype on position 292 of the NA protein in a viral quasispecies population. Neuraminidase inhibition assays using the resistant H7N9 virus showed 100- and 30-fold reduced susceptibility to the two FDA approved inhibitors, oseltamivir and zanamivir, respectively However, unlike known treatments, the novel method of the disclosure is effective against both wildtype Anhui-1 (A/Anhui/1/2013) and also neuraminidase mutant (A/Shanghai/1/2013 with NA-292K) (See FIG. 3). FIG. 3 is a graphical representation showing that ALFERON is effective against both the wildtype Anhui-1 (A/Anhui/1/2013) and also neuraminidase mutant (A/Shanghai/1/2013 with NA-292K; Shanghai 1-NA292K). Antiviral activity of ALFERON was found against both the Shanghai/1/H7N9 and Anhui/1/H7N9; clear inhibition of virus replication was found at 36 and 48 hours post infection. ALFERON with a concentration of 10,000 IU/ml significantly reduced Anhui/1/H7N9 virus load at 36 h post infection, and all three doses (100, 1,000 and 10,000 IU/ml) significantly inhibit replication of oseltamivir sensitive Anhui/1/H7N9 and oseltamivir resistant Shanghai/1/H7N9 at 48 hours post infection. Our data demonstrate that ALFERON is effective against both oseltamivir sensitive and resistant H7N9 viruses.

The methods of the disclosure satisfy the stated need to evolve novel treatments or new synergistic treatments to combat newly uncovered genetically re-assorted viruses, which in some cases, may have become resistant to known treatments.

In one preferred embodiment of the invention, antigenic drift or viral reassortment is reduced in a host animal through the administration α-interferon or more specifically that antigenic drift or viral reassortment in a host animal is prevented or reduced by determining if a host animal has been exposed to or infected by an avian flu virus, administering to the host animal α-interferon.

In another preferred embodiment, the host animal is a human, a pig, a chicken, a turkey, a duck, a bird, a domesticated bird, a bovine, a mammal, a horse, a dog, a goat or another domesticated or non domesticated animal.

In another preferred embodiment, the avian flu virus is selected from the group consisting of NA-292R H7N9, NA-292K H7N9 or a combination thereof.

In another preferred embodiment, the avian flu virus is a combination of NA-292R H7N9, NA-292K H7N9 and at least one more avian influenza virus.

In another preferred embodiment, the α-interferon species were purified as a mixture of at least seven species of α-interferon produced by human white blood cells.

In another preferred embodiment, the seven species of α-interferon comprises α-interferon species α2, α4, α7, α8, α10, α16 and α17.

In another preferred embodiment a host animal infected with influenza A (H7N9) and symptoms of said infection are prevented, treated or reduced by the administration of α-interferon.

In another preferred embodiment symptoms of an NA-292R H7N9 influenza infection, NA-292K H7N9 influenza infection or a viral combination thereof is prevented, treated or reduced by a method comprising the steps of identifying a patient infected with NA-292R H7N9 influenza, NA-292K H7N9 influenza or a combination thereof, detecting in said NA-292R H7N9 influenza, NA-292K H7N9 influenza or said combination thereof neuraminidase-inhibitor resistance and administering to said patient α-interferon.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope any following Examples and the appended claims.

EXAMPLES OF SPECIFIC EMBODIMENTS OF THE INVENTION

Example 1

Oseltamivir (Tamiflu), the first orally active neuraminidase inhibitor commercially developed, was tested on a human lung cell (A549) as a well-known and widely used anti-influenza drug. Confluent A549 cells in 48-well plates were treated with different units of ALFERON (10,000, 1,000 and 100 IU/ml obtained from Hemispherx Biopharma) for 4 hours before infection and untreated cells served as controls; thereafter, both ALFERON treated and untreated A549 cells were infected with the Anhui/1/H7N9 and Shanghai/1/H7N9 viruses at a multiplicity of infection of 0.01 under BSL3/BSL3Ag conditions. Combination of a short natural IFN-a preincubation and a multiplicity of infection of 0.01 simulate the conditions of an in vivo natural infection. A relatively small number of cells are initially infected resulting in the induction of type 1 interferons that in turn induce innate immune responses in uninfected cells. The supernatants were collected at 12, 24, 36 and 48 hour post infection and titrated for virus content. For comparison, oseltamivir was tested against both H7N9 viruses on A549 cells using a concentration of 0.3, 0.2, 0.1 and 0.01 microgram/ml with treatment starting at the time of infection.

Figure 4:
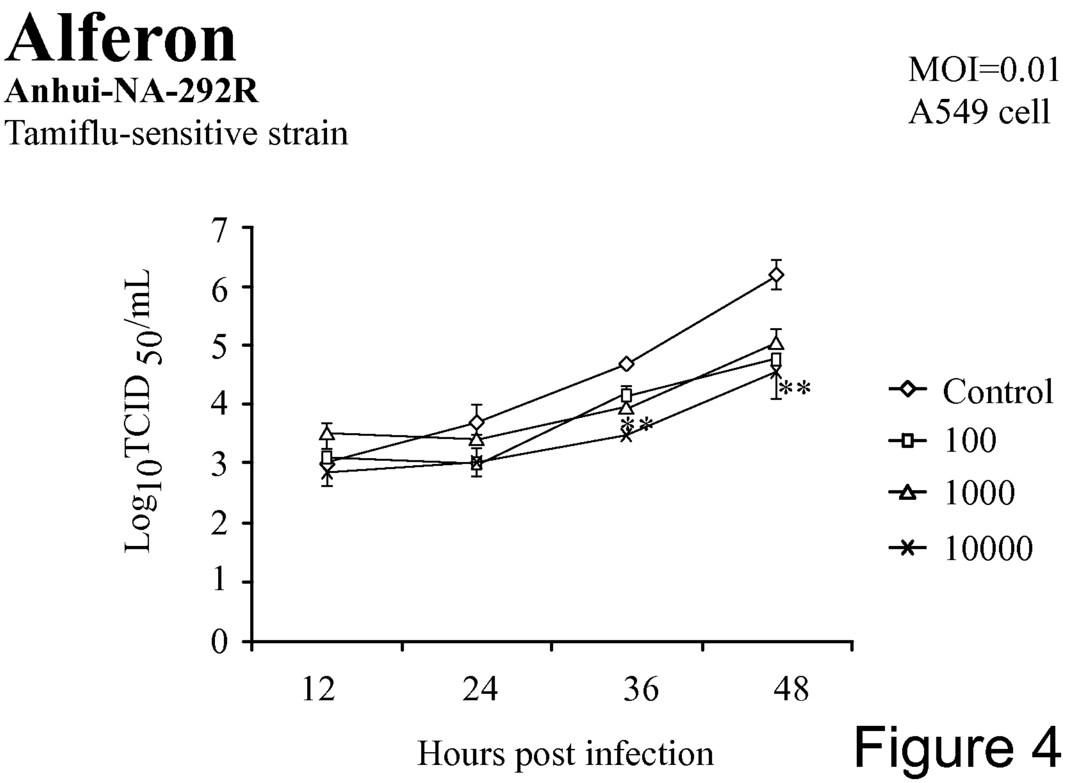
FIG. 4 is a graphical representation showing that ALFERON is effective against wild-type Anhui-1 (A/Anhui/1/2013).
Figure 5:
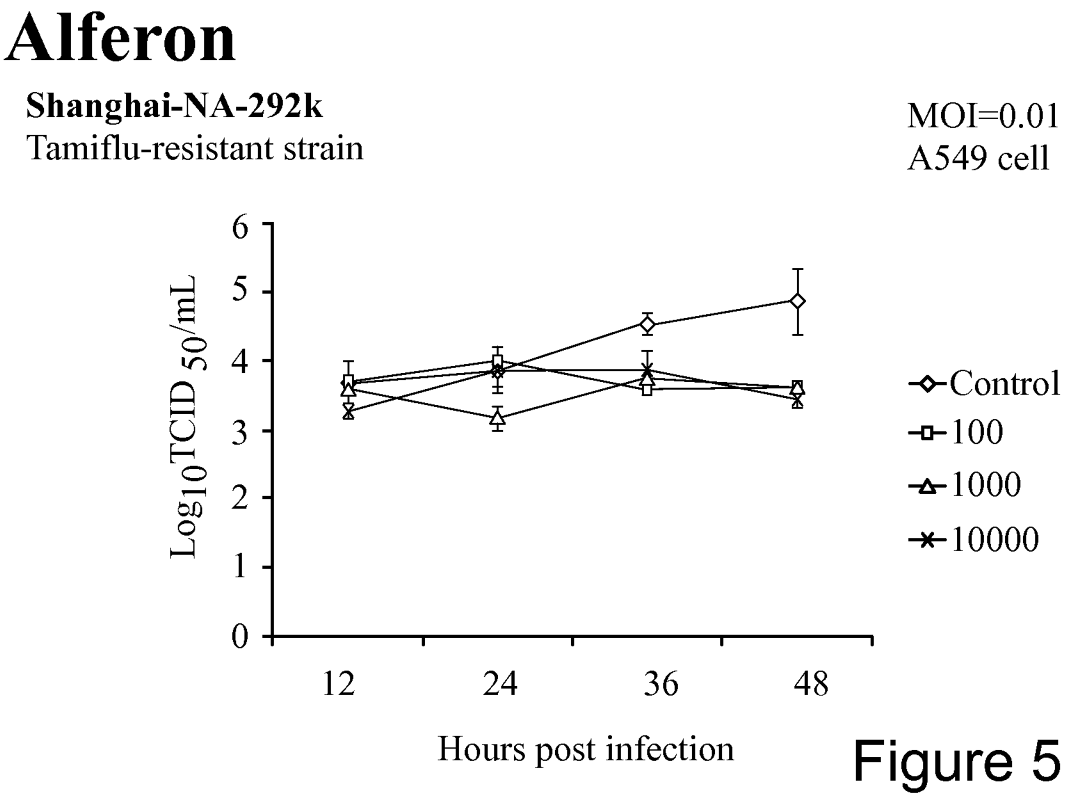
FIG. 5 is a graphical representation showing that ALFERON is also effective against neuraminidase mutant (A/Shanghai/1/2013 with NA-292K; Shanghai 1-NA292K).

The results showed that oseltamivir (Tamiflu) was able to inhibit the replication of NA inhibitor sensitive Anhui/1/H7N9 virus at 36 and 48 hour post infection at a concentration ranging from 0.1 to 0.3 microgram/ml (FIG. 2); in contrast, oseltamivir (Tamiflu) treatment with the same doses did not inhibit the NA inhibitor-resistant Shanghai/1/H7N9 virus (FIG. 3), confirming that the 292K residue in NA of Shanghai/1/H7N9 conferred resistance to oseltamivir. Antiviral activity of ALFERON was found against both the Shanghai/1/H7N9 and Anhui/1/H7N9; clear inhibition of virus replication was found at 36 and 48 h post infection FIGS. 3 and 4). ALFERON with a concentration of 10,000 IU/ml significantly reduced Anhui/1/H7N9 virus load at 36 h post infection, and all three doses (100, 1,000 and 10,000 IU/ml) significantly inhibit replication of oseltamivir sensitive Anhui/l/H7N9 and oseltamivir resistant Shanghai/1/H7N9 at 48 h post infection (FIGS. 3 and 4). Our data demonstrate that ALFERON is effective against both oseltamivir sensitive and resistant H7N9 viruses.

A/Anhui/1/2013 (Anhui/1/H7N9) and A/Shanghai/1/2013 (Shanghai/1/H7N9) were both recently isolated from human cases in China. Sequence information showed that the Anhui/1/H7N9 contains the NA-292R residue and is sensitive to NA inhibitors; in contrast, the Shanghai/1/H7N9 contains a NA-292K residue that is associated with resistance to NA inhibitors. The genetic signatures of both viruses are summarized below in Table B:

TABLE B

| | PB2 | | HA | | NA | M2 | |
|---|---|---|---|---|---|---|---|
| Virus | 627 | 701 | 226[1] | 228[1] | 292[2] | 27 | 31 |
| Anhui/1/H7N9 | K | D | L | G | R[3] | V | N |
| Shanghai/1/H7N9 | K | D | Q | G | K[4] | V | N |

[1]Positions 226, 228 and H3 numbering system.
[2]Position 292 is N2 numbering system.
[3]NA 292 R affords oseltamivir sensitivity
[4]NA 292 K affords oseltamivir resistance Results showed that Tamiflu and ALFERON have significant inhibitory effect on the wild-type A(H7N9) virus. ALFERON but not Tamiflu had an inhibitory effect on oseltamivir-resistant neuraminidase mutant Shanghai 1-NA292K. The results suggest new therapeutic strategies to mitigate the health hazards associated with the infection and the potential pandemic spread of Tamiflu resistant human influenza viruses.

Example 2

Study A: asymptomatic HIV infected subjects with CD4 levels >400 were treated with 500 IU or 1,000 IU of ALFERON in an aqueous buffered solution prepared by diluting ALFERON for injection administered orally daily for 10 days. RNA from peripheral blood leukocytes was isolated from blood collected before, during and post-therapy using Paxgene technology for RNA isolation. A cDNA microarray analysis was utilized to identify genes which were modulated as a result of the ALFERON oral dosing. Study B: normal healthy volunteers being studied in a similar manner.

Initial results in Study A indicate an induction of α-interferon related gene activity in peripheral blood leukocytes following the oral administration of 500 IU or 1,000 IU of a multi-species natural leukocyte α-interferon.

ALFERON used in the study was supplied as a liquid solution packaged in sealed polypropylene lined foil pouches. Each pouch contained 1.0 ml of ALFERON (500 IU or 1,000 IU) or placebo. Solutions were taken orally each day for 10 days. No food or water is taken 30 minutes prior to through 30 minutes after administration. Dosing and blood sampling are shown in Table 1. Dose effects are in Tables 2-4.

TABLE 1

| | Study Day Number and Event | | | | | | | | | | | | | | | | |
|---|---|---|---|---|---|---|---|---|---|---|---|---|---|---|---|---|---|
| | Day Number | | | | | | | | | | | | | | | | |
| | 0* | 1 | 2 | 3 | 4 | 5 | 6 | 7 | 8 | 9 | 10 | 11 | 12 | 13 | 14 | 15 | 16 |
| LDO Dosing | | X | X | X | X | X | X | X | X | X | X | | | | | | |

TABLE 1-continued

Study Day Number and Event

| | Day Number | | | | | | | | | | | | | | | | |
|---|---|---|---|---|---|---|---|---|---|---|---|---|---|---|---|---|---|
| | 0* | 1 | 2 | 3 | 4 | 5 | 6 | 7 | 8 | 9 | 10 | 11 | 12 | 13 | 14 | 15 | 16 |
| Blood Samples Drawn | ↑ B1 + B2 | | ↑ T1 | | | ↑ T2 | | | | | | ↑ T3 | ↑ T4 | | | | ↑ T5 |

*Day 0 = Baseline period in which two separate samples (B1 and B2) are drawn.
Goal: Compare gene expression of T1-T5 Samples to two Baseline Samples Combined (i.e. B1 + B2)

Blood samples were subjected to a cDNA Microarray Analysis as follows:

Array Construction.

The array used in this study comprised a subset of sequence verified cDNA clones from the Research Genetics Inc. 40,000 clone set representing 950 genes containing adenylate/uridylate rich elements and 18 genes potentially involved in AU-directed mRNA decay, 855 ISGs representing an expansion of a previously described clone set containing confirmed and candidate genes stimulated by IFNs in diverse cell types, 288 genes responsive to the viral analog poly(I).poly(C), and 85 housekeeping genes.

Target RNA preparation.

Target RNA was generated in a T7 polymerase based linear amplification reaction. Two μg total RNA and 5 pmol of T7-(dT)24 ("(dT)24" disclosed as SEQ ID NO: 1) primer (5'GGCCAGTGAATTGTAATACGACTCACTATA GGGAGGCGG-(dT)24-3' (SEQ ID NO: 2) in a total volume of 5.5 μl was incubated at 70° C. for 10 min and chilled on ice. For first strand cDNA synthesis, the annealed RNA template was incubated for 1 h at 42° C. in a 10 μl reaction containing first strand buffer (Invitrogen), 10 mM DTT, 1U per μl anti-RNase (Ambion), 500 μM dNTPs and 2 U per μl Superscript II, (Invitrogen). Second strand synthesis was for 2 h at 16° C. in a total reaction volume of 50 μl containing first strand reaction products, second strand buffer (Invitrogen), 250 μM dNTPs, 0.06 U per μl DNA ligase (Ambion), 0.26 U per μl DNA polymerase I, (NEB) and 0.012 U per μl RNase H (Ambion) followed by the addition of 3.3 U of T4 DNA polymerase (3 U per μl; New England Biolabs) and a further 15 min incubation at 16° C. Second strand reaction products were purified by phenol:chloroform:isoamyl alcohol extraction in Phaselock microcentrifuge tubes (Eppendorf) according to manufacturer's instructions and ethanol precipitated. In vitro transcription was performed using the T7 megascript kit (Ambion) according to a modified protocol in which purified cDNA was combined with 1 μl each 10X ATP, GTP, CTP and UTP and 1 μl T7 enzyme mix in a 10 μl reaction volume and incubated for 9 h at 37° C. Amplified RNA was purified using the Rneasy RNA purification kit (Ambion).

RNA labeling. Cy3 or Cy5 labeled cDNA was prepared by indirect incorporation. Two μg of amplified RNA, 1 μl dT12-18 primer (SEQ ID NO: 3) (1 μg per μl, Invitrogen), 2.6 μl random hexanucleotides (3 μg per μl, Invitrogen) and 1 μl anti-RNAse (Ambion) were combined in a reaction volume of 15.5 μl and incubated for 10 min at 70° C. Reverse transcription was for 2 h at 42° C. in a 30 μl reaction containing annealed RNA template, first strand buffer, 500 mM each dATP, dCTP, dGTP, 300 μM dTTP, 200 μM aminoallyl-dUTP (Sigma), 10 mM DTT, 12.7 U per μl Superscript II. For template hydrolysis, 10 μl of 0.1M NaOH was added to the reverse transcription reaction and the mixture was incubated for 10 min at 70° C., allowed to cool at room temperature for 5 min and neutralized by addition of 10 μl 0.1M HCl. cDNA was precipitated at— 20° C. for 30 min after addition of 1 μl linear acrylamide (Ambion), 4 μl 3M NaAc (pH 5.2) and 100 μl absolute ethanol then resuspended in 5 μl of 0.1M NaHCO 3. For dye-coupling the contents of 1 tube of NHS ester containing Cy3 or Cy5 dye (Amersham Biosciences) was dissolved in 45 μl DMSO. Five μl dye solution was mixed with the cDNA and incubated for 1 h in darkness at room temperature. Labeled cDNA was purified on a Qiaquick PCR purification column (Qiagen) according to manufacturer's instructions. Eluted cDNA was dried under vacuum and resuspended in 30 μl of Slidehyb II hybridization buffer (Ambion). After 2 min denaturation at 95° C. the hybridization mixture was applied to the microarray slide under a coverslip. Hybridization proceeded overnight in a sealed moist chamber in a 55° C. waterbath. Post-hybridization, slides were washed successively for 5 min each in 2×SSC 0.1% SDS at 55° C., then 2×SSC at 55° C. plus a final 5 min wash in 0.2×SSC at room temperature.

Data Acquisition and Normalization.

Data were acquired with a GenePix 4000B laser scanner and GenePix Pro 5.0 software. Raw data were imported into GeneSpring 6.0 software (Silicon Genetics) and normalized based on the distribution of all values with locally weighted linear regression (LOESS) before further analysis.

Initial results in Study A indicate that orally administered ALFERON was well tolerated at the 500 and 1,000 IU/day dosage levels. cDNA microarray analysis identified 385 genes that were expressed >two fold over baseline in two or more patient samples. As shown in Tables 2, 3 and 4 an approximately four fold increase in gene expression was seen at the 1,000 IU/day dosage level compared to 500 IU/day ($p<0.0001$). Although, not an exhaustive list, Table 5 shows 25 genes that were expressed >two fold over baseline in ≥33% of patient samples. PDZ and LIN domain 5 and 2'-5' oligoadenylate synthetase-like were among the top five upregulated genes. 2'-5' oligoadenylate synthetase is an important component of the interferon intracellular antiviral pathway. Importantly, as shown in Table 6, genes related to activation of an inflammatory response such as tumor necrosis factor (TNF) related genes were down regulated.

Recent evidence shows that the virulence of some influenza A isolates correlates with the ability of the nonstructural NS1 viral protein to bind to human PDZ domains and thereby abrogating the expression of antiviral genes in host cells including interferon pathways (Science xpress, 26 Jan. 2006). Thus, the finding that orally administered ALFERON can upregulate PDZ domain expression raises the possibility that ALFERON could have an important role in abrogating the ability of influenza viruses to evade human host defense mechanisms.

The orally administered ALFERON was well-tolerated with no serious adverse events reported. Only several mild adverse events were reported, such as a metallic taste in mouth or flatulence/bloating. There were no clinically significant changes in laboratory parameters and no changes in Karnofsky Performance Status (KPS).

Experiments to date indicate that a biological cocktail of natural human interferon species administered orally has systemic biological activity based on upregulation of α-interferon related genes in peripheral blood leukocytes. Because alpha α-interferon are broad spectrum antiviral/immunomodulatory molecules, potential applications in numerous α-interferon-sensitive diseases exist, including application to respiratory infections such as avian influenza.

Our results, suggest that ALFERON may have significant inhibitory effect on the wild-type A(H7N9) virus, a triple reassortant virus carrying genes from various influenza A viruses including H7N3, H9N2 and H11N9 or H2N9 as well as oseltamivir-resistant neuraminidase mutant Shanghai 1-NA292K. These findings coupled with finding above regarding the use of ALFERON for abrogating the ability of influenza viruses to evade human host defense mechanisms also suggest new therapeutic strategies to mitigate the health hazards associated with the infection and the potential pandemic spread of new drug resistant human influenza viruses.

TABLE 2

Dose Effect: Number of Genes with Expression Increased ≥2 Fold Over Baseline in Two or More Patient Samples

| | Dose | | | | | | | | Fold |
|---|---|---|---|---|---|---|---|---|---|
| | 500 IU | | | | 1,000 IU | | | | Increase |
| Patient # | 1 | 2 | 3 | Mean | 4 | 5 | 6 | Mean | of Mean |
| Day 2 | 10 | 1 | 39 | 16.7 | 85 | 77 | 108 | 90 | 5.4 |
| Day 5 | 14 | 4 | 23 | 13.7 | 54 | 72 | 35 | 54 | 3.9 |
| Day 11 | 1 | 8 | 4 | 4.3 | 4 | 45 | 40 | 30 | 6.9 |
| Day 12 | 3 | 15 | — | 9.0 | 19 | 44 | 28 | 30 | 3.4 |
| Day 16 | — | 14 | — | 14 | 3 | 59 | 48 | 37 | 2.6 |
| Mean | 7.0 | 8.4 | 22 | 12.5 | 33 | 59 | 52 | 48 | 3.9 |

Student's t-test, p-value <0.0001 (n = 385)

TABLE 3

Dose Effect: Number of Genes with Expression Increased ≥2 Fold Over Baseline in Three or More Patient Samples

| | Dose | | | | | | | | Fold |
|---|---|---|---|---|---|---|---|---|---|
| | 500 IU | | | | 1,000 IU | | | | Increase |
| Patient # | 1 | 2 | 3 | Mean | 4 | 5 | 6 | Mean | of Mean |
| Day 2 | 3 | 1 | 19 | 7.6 | 36 | 41 | 42 | 39.7 | 5.2 |
| Day 5 | 2 | 2 | 6 | 3.3 | 16 | 17 | 16 | 16.3 | 4.9 |
| Day 11 | 1 | 1 | 1 | 1.0 | 3 | 3 | 3 | 3.0 | 3.0 |
| Day 12 | 1 | 2 | — | 1.5 | 7 | 8 | 8 | 7.7 | 5.1 |
| Day 16 | — | 0 | — | 0 | 2 | 2 | 2 | 2.0 | >5 |
| Mean | 1.8 | 1.2 | 8.7 | 3.9 | 12.8 | 14.2 | 14.2 | 13.7 | 3.5 |

Student's t-test, p-value <0.0001 (n = 252)

TABLE 4

Dose Effect: Number of Genes with Expression Increased ≥3 Fold Over Baseline in Two or More Patient Samples

| | Dose | | | | | | | | Fold |
|---|---|---|---|---|---|---|---|---|---|
| | 500 IU | | | | 1,000 IU | | | | Increase |
| Patient # | 1 | 2 | 3 | Mean | 4 | 5 | 6 | Mean | of Mean |
| Day 2 | 0 | 0 | 9 | 3.0 | 23 | 10 | 37 | 23.0 | 7.8 |
| Day 5 | 5 | 1 | 5 | 3.7 | 16 | 19 | 4 | 13.0 | 3.5 |
| Day 11 | 1 | 2 | 0 | 1.0 | 0 | 14 | 3 | 5.7 | 5.7 |
| Day 12 | 1 | 3 | — | 2.0 | 3 | 10 | 2 | 5.0 | 2.5 |
| Day 16 | — | 0 | — | 0.0 | 0 | 14 | 6 | 6.7 | >5 |
| Mean | 1.8 | 1.2 | 4.7 | 2.6 | 8.4 | 13.4 | 10.4 | 10.7 | 4.1 |

Student's t-test, p-value <0.0001 (n = 69)

TABLE 5

Genes Expressed ≥ Two Fold Over Baseline in ≥ 33% of Patient Samples

| | | Expression Frequency (%) | | |
|---|---|---|---|---|
| | Identified Gene | 500 IU | 1,000 IU | Overall |
| 1 | SFRS protein kinase 1 | 83 | 40 | 59 |
| 2 | *Homo sapiens*, clone image: 5164031, mRNA | 17 | 87 | 56 |
| 3 | PDZ and LIN domain 5 | 0 | 93 | 52 |
| 4 | Interleukin 17 receptor | 0 | 93 | 52 |
| 5 | 2'-5' oligoadenylate synthetase-like | 33 | 67 | 52 |
| 6 | Similar to KIAA0160 gene product | 0 | 87 | 48 |
| 7 | N-myristoyltransferase 2 | 0 | 80 | 44 |
| 8 | Proteasome (prosome, macropain) 265 subunit, ATPase, 6 | 0 | 73 | 41 |
| 9 | Coagulation factor II (thrombin) receptor | 0 | 73 | 41 |
| 10 | Cytochrome P450, family 51, subfamily A, polypeptide | 0 | 73 | 41 |
| 11 | Interferon induced transmembrane protein 2 | 33 | 47 | 41 |
| 12 | Major histocompatibility complex, class I, F | 33 | 47 | 41 |
| 13 | Sarcoglycan, beta (43 kDa dystrophin-associated glycoprotein) | 0 | 73 | 41 |
| 14 | Glutamate dehydrogenase 1 | 0 | 73 | 41 |
| 15 | FGG | 0 | 67 | 37 |
| 16 | Coagulation factor III (thromboplastin, tissue factor) | 0 | 67 | 37 |
| 17 | Interferon (alpha, beta, and omega) receptor 1 | 0 | 67 | 37 |
| 18 | Ribosomal protein S6 kinase, 90 KDa, polypeptide 3 | 0 | 60 | 33 |
| 19 | Hemoglobin, epsilon 1 | 33 | 33 | 33 |
| 20 | Acyl-coenzyme A dehydrogenase, short/branched chain | 0 | 60 | 33 |
| 21 | Hypothetical protein MGC20481 | 17 | 47 | 33 |
| 22 | RAB7, member RAS oncogene family | 17 | 47 | 33 |
| 23 | Ribosomal protein S15a | 0 | 60 | 33 |
| 24 | Glutamate dehydrogenase I | 0 | 60 | 33 |
| 25 | Small nuclear RNA activating complex, polypeptide 3, 50 KDa | 25 | 40 | 33 |

TABLE 6

Five Tumor Necrosis Factor (TNF) Related Genes with a 50% or Greater Reduction in Expression

| | |
|---|---|
| 1. | TNF (ligand) superfamily, member 11 |
| 2. | TNF receptor superfamily, member 6b, decoy |
| 3. | TNF receptor - associated factor 1 |

TABLE 6-continued

| Five Tumor Necrosis Factor (TNF) Related Genes with a 50% or Greater Reduction in Expression | |
|---|---|
| 4. | TNF, alpha-induced protein 6 |
| 5. | TNF receptor superfamily, member 10b |

Example 3

Optionally, ALFERON LDO can be administered before, during or after the administration of mismatched dsRNA, such as AMPLIGEN®

AMPLIGEN, a mismatched dsRNA, may be of the general formula rInr(C11-14U)n ("rIn" disclosed as SEQ ID NO: 4), which is preferably rInr($C_{12}$U)n ("rIn" disclosed as SEQ ID NO: 4 where n is an integer having a value of from 40 to 40,000. In this and the other formulae that follow r=ribo. Other mismatched dsRNAs for use in the present invention are based on co-polynucleotides selected from poly (Cm,U) and poly (Cm,G) in which m is an integer having a value of from 4 to 29 and are mismatched analogs of complexes of polyriboinosinic and polyribocytidilic acids, formed by modifying rIn•rCn to incorporate unpaired bases (uracil or guanine) along the polyribocytidylate (rCm) strand. Alternatively, the dsRNA may be derived from r(I)•(C) dsRNA by modifying the ribosyl backbone of polyriboinosinic acid WO, e.g., by including 2'-O-methyl ribosyl residues. The mismatched may be complexed with an RNA-stabilizing polymer such as lysine cellulose. Of these mismatched analogs of rIn•rCn, the preferred ones are of the general formula rIn•r(C11-14,U)n or rIn•r(C29,G)n, and are described by Ts'o & Carter in U.S. Pat. Nos. 4,024,222 and 4,130,641; the disclosures of which are hereby incorporated by reference. The dsRNAs described therein are generally suitable for use according to the present invention.

Furthermore, dsRNAs of the following general formulas are also envisioned:

$r(I)\cdot r(C4,U)$, $r(I)\cdot r(C7,U)$, $r(I)\cdot r(C13,U)$, $r(I)\cdot r(C22,U)$, $r(I)\cdot r(C20,G)$ and $r(I)\cdot r(Cp\cdot 23,G>p)$.

A neuraminidase-inhibitor resistant reassortant Anhui/1 virus (Anhui 1/NA R292K) is generated by standard reverse genetics methods currently used and is confirmed by sequencing (Liu et al. at Kansas State University). The mutation will be confirmed by sequencing (cDNA). A/Anhui/1/2013, reverse genetically created WT H7N9 (226L/627K), and the neuraminidase-inhibitor resistant reassortant Anhui/1 virus (Anhui 1/NA R292K) are tested against a number of traditional drugs as well as rintatolimod, interferon-α n3 and a synergistic combination.

Early administration of ALFERON LDO in combination with a dsRNA, namely AMPLIGEN, can produce an unexpected synergistic effect against a viral challenge.

Determination of the antiviral activity of rintatolimod (AMPLIGEN) and α-interferon-n3 (ALFERON N) is accomplished in quadruplicate (minimum replications or higher) using serial 2-fold titrations of drugs covering minimally the ranges 1,000 to 10,000 IU/ml of α-interferon and 10 μg to 3,000 μg/ml of rintatolimod. The rintatolimod administered may be within 10 μg to 15,000 μg per dose and may be of oral, intranasal, intravenous, subcutaneous, or intramuscular administration. Oseltarmivir (Tarmivir) and Ribavirin (known also as Rebetol, Copegus, Virazole) can also be tested in the minimum range of 0.01 to 0.30 μg/ml and 1.0 to 30 μg/ml, respectively.

Initial dose ranging experiments can establish the optimal TCID50 (tissue culture infectious dose-50) for use in subsequent efficacy experiments. It is anticipated that infectious virus at $10^2$ or $10^3$ TCID50 following a −18 hour and a zero time drug pre-incubation is optimal. Assay of antiviral activity are subsequently evaluated by CPE (visual observation and vital dye uptake quantitative assay) and antiviral titers by qPCR and end-point infectious viral titers. Non-virus infected wells are used to estimate drug toxicity. Due to species specific barriers interferon requires a primate cell line such as A549 (human lung carcinoma), MDCK (Madin-Darby Canine Kidney) is acceptable for rintatolimod. For pre-incubation studies replace with fresh drug at the time of infection. Vero cells are genetically deficient for human type-1 IFNs and are used as a negative control for the molecular action of rintatolimod via the TLR3 induction or the induction of antiviral cellular type-1 IFNs.

Based on the observed single agent antiviral activity, synergy assays between rintatolimod (AMPLIGEN) and interferon-a n3 (ALFERON) are accomplished in a 96 or 24-well format as appropriate on A549 cells. Serial two-fold dilutional titrations are initiated beginning at 10× the established minimum inhibitory concentration for each agent. The combination index is determined by the median effect method of Chou and Talalay and results are illustrated by dose-effect, median-effect, isobolograms and combination index-effect. A second assay can be performed with human embryonic kidney HEK 293T to additionally verify any initial findings.

All patents, patent applications, and references cited anywhere in this disclosure are hereby incorporated by reference in their entirety.

We claim:

1. A method for reducing antigenic drift or viral reassortment in a human comprising determining if the human has been exposed to or infected by an avian influenza virus, and administering to the exposed or the infected human α-interferon;

wherein the α-interferon comprises seven species of α-interferon comprises α-interferon species α2, α4, α7, α8, α10, α16 and α17;

wherein the α-interferon is administered intravenously, subcutaneously, intramuscularly, or intranasally.

2. The method of claim 1 wherein the avian influenza virus is selected from the group consisting of NA-292R H7N9, NA-292K H7N9 or a combination thereof.

3. The method of claim 1 wherein the avian influenza virus is a combination of NA-292R H7N9, NA-292K H7N9 and at least one more avian influenza virus.

4. The method of claim 1 wherein the α-interferon species were purified as a mixture of at least seven species of α-interferon produced by human white blood cells.

5. The method of claim 1, wherein the α-interferon administered is within a concentration of at least within 1,000 IU/ml to 10,000 IU/ml.

6. The method of claim 1, wherein the α-interferon administered is within 1,000 IU to 10,000,000 IU per dose.

* * * * *